United States Patent [19]

Calvet et al.

[11] Patent Number: 5,236,947
[45] Date of Patent: Aug. 17, 1993

[54] PROPANAMINES, THEIR PHARMACOLOGICAL PROPERTIES AND THEIR APPLICATION AS AN ANTIDIARRHEAL

[75] Inventors: Alain Calvet, L'Hay-Les-Roses; Agnes Grouhel, Meudon; Henri Jacobelli, Paray Vieille Poste; Jean-Louis Junien, Sevres; Xavier Pascaud, Paris, all of France

[73] Assignee: Jouveinal S.A., Paris, France

[21] Appl. No.: 899,712

[22] Filed: Jun. 17, 1992

Related U.S. Application Data

[62] Division of Ser. No. 660,873, Feb. 26, 1991, Pat. No. 5,143,938.

[30] Foreign Application Priority Data

Feb. 28, 1990 [FR] France .................. 90 02495

[51] Int. Cl.⁵ .............. A61K 31/385; A61K 31/39; A61K 31/335
[52] U.S. Cl. .................. 514/433; 514/439; 514/452; 549/35; 549/369
[58] Field of Search .............. 549/35, 369; 514/452, 514/433, 439

[56] References Cited

U.S. PATENT DOCUMENTS 3,182,084  5/1965  Wilson et al. .......... 564/342
3,714,159  1/1973  Janssen et al. .......... 544/130

*Primary Examiner*—Alan L. Rotman
*Assistant Examiner*—A. A. Owens
*Attorney, Agent, or Firm*—Bacon & Thomas

[57] ABSTRACT

The present invention relates to propanamines of general formula (I)

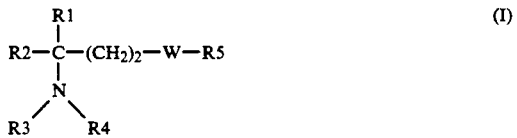

in which:

R1 is a phenyl radical optionally mono-, di- or trisubstituted in an identical or different manner with halogen atoms, or lower alkyl, lower haloalkyl or lower alkoxy radicals;

R2 is a lower alkyl radical,

R3 and R4 are a hydrogen atom or a lower alkyl, lower alkenyl or lower cycloalkyalkyl radical, R5 is a 5-to 7-membered cycloalkyl radical or a phenyl radical, and W represents a heterocycle $=C[Q-(CH_2)_n-Q]$ in which Q is an oxygen or sulfur atom and n is 2 or 3, and their acid addition salts with pharmaceutically acceptable acids. The invention also relates to antidiarrheal pharmaceutical compositions comprising the claimed propanamines.

6 Claims, No Drawings

PROPANAMINES, THEIR PHARMACOLOGICAL PROPERTIES AND THEIR APPLICATION AS AN ANTIDIARRHEAL

This application is a division of application Ser. No. 07/660,873, filed Feb. 26, 1991 now U.S. Pat. No. 5,143,938.

The present invention relates to novel propanamines, to their pharmacological properties and to their application for therapeutic purposes, in particular as antidiarrheals.

For a long time, morphine and its derivatives have been used as antidiarrheals in spite of their harmful side effects.

To remedy this state of affairs, the search for synthetic compounds having more selective activity has led to the development of molecules which are active on intestinal peristalsis, such as diphenoxylate (INN) and, more recently, loperamide (INN) which is 4-(4-chlorophenyl)-4-hydroxy-N,N-dimethyl-α,α-diphenyl-1-piperidinebutanamide.

In fact, these compounds are related to meperidine (INN), which is an analgesic known to be of the morphine type (The Pharmaceutical Basis of Thera-peutics Goodman and Gilman's - 6th Ed. 1980 - p. 513–518). Thus, when taken in excessive amounts, these antidiarrheal compounds can cause adverse side effects such as dependency symptoms, or a disproportionate increase in intestinal transit time which can have dramatic consequences: constipation, then, more seriously, distention and, in extreme cases, perforation of the intestine (Textbook of Pharmacology - W. C. Bowman and M. J. Rand, 2nd Ed. 1980, p. 25–36 and 25–40).

In point of fact, propanamines have now been found which possess considerable advantages for the treatment of diarrhea states of diverse etiologies. In effect, regardless of their low toxicity and their unquestionable activity when administered orally in this pathology, they are, even at high dose, practically devoid of effects on the gastrointestinal transit time of the rat and do not induce a dependency phenomenon in mice.

The propanamines of the invention correspond to the general formula (I)

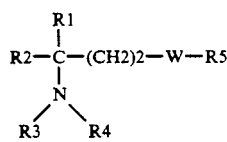

in which:

R1 is a phenyl radical optionally mono-, di- or trisubstituted in an identical or different manner with halogen atoms or lower alkyl, lower haloalkyl or lower alkoxy radicals, or is a 5- or 6-membered monocyclic heteroaryl radical in which the single heteroatom is nitrogen, oxygen or sulfur, R2 is a lower alkyl radical, R3 and R4 are a hydrogen atom or a lower alkyl, lower alkenyl or lower cycloalkylalkyl radical, and are different or identical without, however, both being lower cycloalkylalkyl , or, together with the nitrogen atom to which they are attached, form a saturated 5- to 6-membered heterocycle comprising only one heteroatom, R5 is a 5- to 7-membered cycloalkyl radical, a phenyl radical or a 5- or 6-membered monocyclic heteroaryl radical in which the single heteroatom is nitrogen, oxygen or sulfur, which radicals are optionally mono-, di- or trisubstituted in an identical or different manner with halogen atoms or lower alkyl, lower haloalkyl or lower alkoxy radicals, and W represents a group =CH—QH, or a heterocycle =C[Q—(CH2)n—Q], or a group =C=Q, in which groups Q is an oxygen or sulfur atom, n has the value 2 or 3, W being =C=Q only when R3 and R4 are not both hydrogen.

The propanamines of the invention contain at least one asymmetric carbon atom responsible for enantiomeric forms, which are included in the invention on the same basis as the racemic forms.

The invention also relates to the addition salts of the propanamines with inorganic or organic acids, and especially with those which are pharmaceutically acceptable.

For this purpose, the salts with hydrochloric acid and maleic acid are the ones most used; however, addition salts which are also acceptable are obtained with acetic, benzenesulfonic, camphorsulfonic, citric, ethanesulfonic, fumaric, hydrobromic, lactic, malic, methanesulfonic, mucic, nitric, pamoic, phosphoric, salicylic, stearic, succinic, sulfuric and tartaric acids.

Except where expressly stated to the contrary, the lower alkyl, alkenyl, haloalkyl or alkoxy radicals comprise from 1 to 4 carbon atoms and the cycloalkyl radicals from 3 to 7 carbon atoms, the halogen atoms are essentially fluorine, chlorine and bromine and the phenyl radicals, when substituted, are preferably substituted in the meta and para positions.

In the interest of clarification of the text which follows, and to facilitate the structural classification of the compounds of the invention, i) according to the meanings specified above for W, the propanamines (I) are included:

in a group "A" when W is a group =CH—QH, in a group "D" when W is a heterocycle =C[Q—(CH2)n—Q], in a group "C" when W is a group =C=Q, and this is illustrated by the formulae:

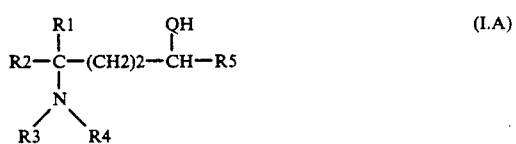

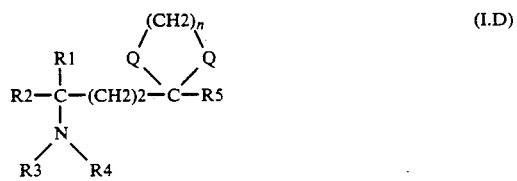

-continued

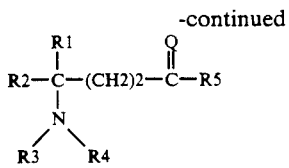
(I.C)

ii) and, for each group mentioned, as a third character, the index 1 appears when R3 and R4 in the propanamine are both hydrogen, this being, moreover, ruled out when W represents the group =C=Q, the index 2 appears when only one of R3 or R4 represents hydrogen, the index 3 appears when R3 and R4 are both other than hydrogen, iii) finally, when it is expressly necessary to indicate the identity of the atom Q, a final index /O or /S gives this information.

In the set of propanamines (I), preference is given to those in which R1 is a phenyl radical, optionally mono- or disubstituted, R2 is a linear lower alkyl radical, R3 and R4, which may be identical or different, are a hydrogen atom or a lower alkyl, a lower alkenyl or lower cycloalkylalkyl radical, R5 is a phenyl radical, optionally substituted, and, among these, the propanamines (I) in which W represents groups in which Q is an oxygen atom and n has the value 2, and thereafter W being 1,3-dioxolane-2,2-diyl (formulae belonging to group I.D).

or represents a group =C=Q in which Q is oxygen, R3 and R4 not both being hydrogen (formulae I.C.2/0 or I.C.3/0).

Special preference is given to the compounds of formula (I.D.2) which comprises the products in which W is 1,3-dioxolane-2,2-diyl, R3 is a lower alkyl or lower cycloalkylalkyl radical and R4 is hydrogen, and among these the compound described in Example 3.f, which is the 2-[3-N-Methylamino-3-(4-trifluoromethylphenyl)-pentan-1-yl]-2-(3,4,5-trimethoxyphenyl)1,3-dioxolane, and the compounds of formula (I.C.3/0) in which W is carbonyl and R3 and R4, which may be identical or different, are lower alkyl.

Among these, preference is given to the propanamine (I) described in Example 9.b.2, which is 4-N,N-Dimethylamino-4-(4-methylphenyl)-1-(3,4,5-trimethoxyphenyl)-hexan-1-one.

The invention also relates to a process for preparing the propanamines (I) which is illustrated in schemes below, consisting:

A - for preparing a propanamine in which R3 and R4 are hydrogen, and as shown in Scheme 1, A.1 - in reducing the group =C=Q of a nitro precursor of formula (II)

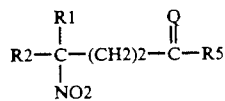
(II)

with a metal hydride or organometallic hydride (Hm.3) of general formula (Hm)

M1(t) M2H(r)Rx(s)(Hm)

in which

M1 is an alkali metal such as lithium or sodium and of which the representative index (t) has the value 0 or 1, M2 is an element of group III of the Periodic Classification, such as aluminum or boron, (r) is the representative index for the number of hydrogen atoms of the hydride and having the values 1, 2, 3 or 4, Rx is a carbonitrile group or a lower alkyl or alkoxy radical and of representative index (s) having values 0, 1, 2 or 3, and of which the indices correspond to the equation:

(r)+(s)−(t)=3 and for which, in the hydrides (Hm.3), it is preferable that M2 is boron and, when (s) has the value 1, it is a carbonitrile to obtain an intermediate (III)

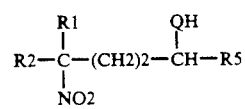
(III)

which is reduced by a hydrogenation catalyzed by a metal of group VIII of the Periodic Classification or one of their oxide or alternatively one of their salt, and preferably by platinum, palladium or nickel and their derivatives mentioned above, and more especially for nickel, its alloys with aluminum as in Raney alloy, to obtain a propanamine (I.A.1)

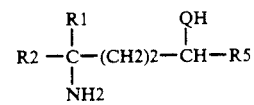
(I.A.1)

A.2 - in condensing a bifunctional reagent HQ-(CH2)n-QH in which Q is oxygen or sulfur, and n has the values 2 or 3, with the precursor (II) described above, to obtain a heterocyclic intermediate (IV)

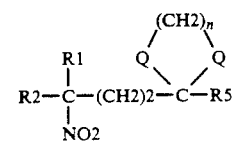
(IV)

which is reduced by a hydrogenation catalyzed by the elements of group VIII specified above to a propanamine (I.D.1)

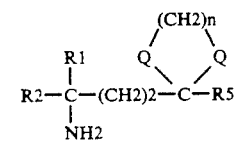
(I.D.1)

SCHEME 1

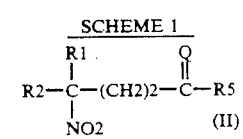
(II)

-continued
SCHEME 1

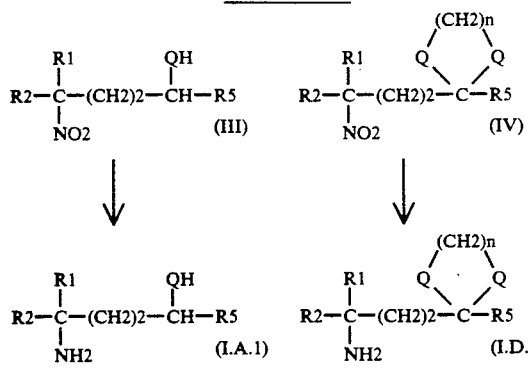

B - and, for preparing a propanamine in which R4, different from R3, is hydrogen, the process consists, as shown in Scheme 2:

B.1- in alkylating a propanamine (I) of formula (I.A.1) or of formual (I.D.1) with an alkylating reagent R3X1 in which X1 is a halogen atom such as chlorine, bromine or iodine, to obtain a propanamine (I.A.2) or a propanamine (I.D.2), respectively

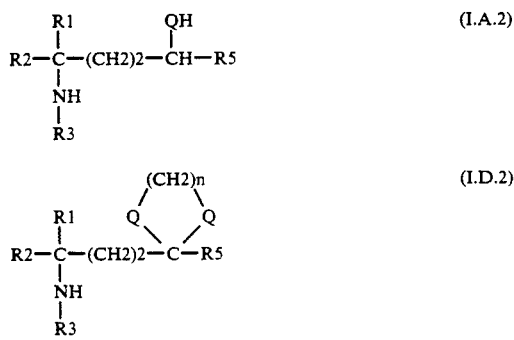

B.2 - in acylating a propanamine (I) of formula (I.A.1) or of formula (I.D.1) with a reagent (R6CO)p2 in which R6 is hydrogen or a carbon-based homologous radical smaller by one carbon atom than R3 (R3=CH2—R6), and X2 is, when p is equal to 1, a halogen atom such as chlorine or bromine or a hydroxyl radical, and, when p is equal to 2, is an oxygen atom, to obtain an N-carboxamide intermediate (V.A2) or an N-carboxamide intermediate (V.D.2)

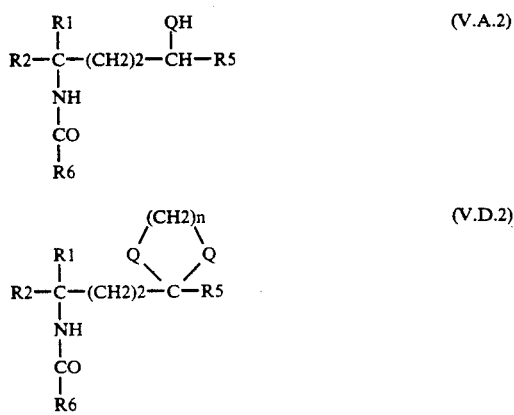

SCHEME 2
Group A: W = =C=Q;
Group D: W = =C[Q—(CH2)n—Q]

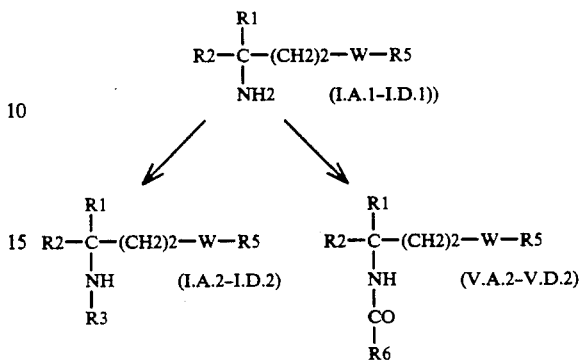

which is reduced with a metal hydride or organometallic hydride (Hm.2) of formula (Hm) defined above and in which M2 is aluminum and, when it represents boron, (r) has the value 3 and (t) has the value 0, to obtain a propanamine (I.A.2) or a propanamine (I.D.2) described above, respectively B.3 - and, either in oxidizing with a diatomic species or a polyatomic ion whose standard redox potential E⁰ is greater than 0.60 V a propanamine (I.A.2) in which Q is oxygen, or in hydrolyzing with an acid solution and/or oxidizing solution a propanamine (I.D.2), to obtain a propanamine (I.C.2) in which Q is oxygen and of formula (I.C.2/0)

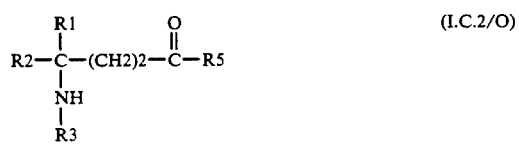

B.4 - and, for preparing a propanamine in which Q is sulfur and of formula (I.C.2/S)

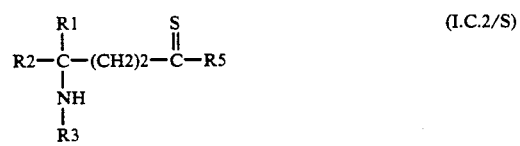

either in reacting the propanamine (I.C.2/0) with a reagent Rz-NH2 in which Rz is hydrogen or a primary amine or hydroxyl function or alternatively a lower alkyl or phenyl radical, to obtain an intermediate compound (VI.1)

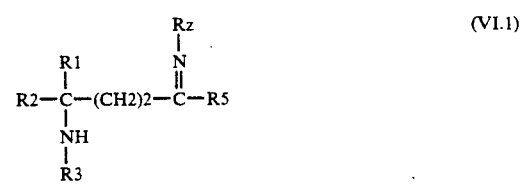

SCHEME 3

R2—C(R1)(NHR3)—(CH2)2—CH(OH)—R5 (I.A.2/O)

R2—C(R1)(NHR3)—(CH2)2—C(R5)(Q-(CH2)n-Q) (I.D.2)

↓

R2—C(R1)(NHR3)—(CH2)2—C(=O)—R5 (I.C.2/O)

↙ ↘

R2—C(R1)(NH R3)—(CH2)2—C(=N-Rz)—R5 (VI.1) → R2—C(R1)(NHR3)—(CH2)2—C(=S)—R5 (I.C.2/S)

which is employed in a thioxo substitution reaction with hydrogen sulfide or carbon disulfide or sulfur monochloride or alternatively with an S-alkylthioic or S-phenylthioic acid, or in reacting the propanamine (I.C.2/O) with phosphorous pentasulfide, to obtain the compound (I.C.2/S).

C - and, for preparing a propanimine (I) in which R3 and R4 are not hydrogen,

C.1- and, when R3 and R4, identical, are lower alkyl or alkenyl, in dialkylating a propanamine (I) of formula (I.A.1) or of formula (I.D.1) with an aldehyde R7CHO in which R7 is hydrogen or a carbon-based homologous alkyl or alkenyl radical comprising oen carbon atom less than R3 and R4 (R3=R4=—CH2—R7), and with a reducing agent which is a metal hydride or organometallic hydride (Hm.3) defined above or alternatively formic acid or one of its salts, to obtain, depending on the starting propanamine employed, either a propanamine (I.A.3) or a propanamine (I.D.3) as shown in Scheme 4,

R2—C(R1)(NR3R4)—(CH2)2—CH(OH)—R5 (I.A.3)

R2—C(R1)(NR3R4)—(CH2)2—C(R5)(Q-(CH2)n-Q) (I.D.3)

C.2 - and, when R3 and R4, together and with the nitrogen atom to which they are attached, form a saturated 5-to 6-membered heterocycle, and as shown in Scheme 4, in dialkylating a propanamine (I.D.1) with a dihalogenated reagent X3—(CH2)q—X4 in which X3 and X4, which may be identical or different, are chlorine, bromine or iodine and q has the value 4 or 5.

SCHEME 4

R2—C(R1)(NH2)—(CH2)2—CH(OH)—R5 (I.A.1)

R2—C(R1)(NH2)—(CH2)2—C(R5)(Q-(CH2)n-Q) (I.D.1)

+R7—CHO +reducing agent ↓

+X3—(CH2)q—X4 ↘

R2—C(R1)(NR3R4)—(CH2)2—CH(OH)—R5 (I.A.3) (R3 = R4)

R2—C(R1)(NR3R4)—(CH2)2—C(R5)(Q-(CH2)n-Q) (I.D.3) (R3 = R4)

R2—C(R1)(N-(CH2)q)—(CH2)2—C(R5)(Q-(CH2)n-Q) (I.D.3)

C.3 - and for preparing a propanamine (I) in which R3 and R4, different, are not hydrogen, and i) - of formula (I.D.3) or of formula (IC.3)

R2—C(R1)(NR3R4)—(CH2)2—C(=O)—R5 (I.C.3)

in alkylating a propanamine (I) of formula (I.D.2) or formula (I.C.2) in which R4 is hydrogen, with an alkylating reagent R4 X5 in which R4 is lower alkyl, lower alkenyl or lower cycloalkylalkyl, and X5 is a chlorine, bromine or iodine atom, and ii) - of formula (I.A.3) or of formula (I.D.3), in reacting a propanamine (I.A.2) or a propanamine (I.D.2) with an aldehyde R7-CHO defined above and which is a homologue smaller by one carbon atom than R4 (R4=—CH2-R7) and a reducing agent as defined above, or iii) in acylating a propanamine (I.A.2) or a propanamine (I.D.2) with an acylating reagent R9-COX6 in which R9 is hydrogen or a homologous carbon-based radical smaller by one carbon atom than R4 (R4=—CH2-R9) and X6 is a chlorine or bromine atom or alternatively a hydroxyl radical, to obtain the corresponding N-carboxamides (V.A.3) and (V.D.3)

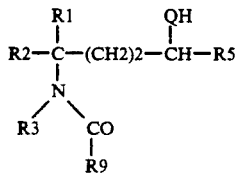
(V.A.3)

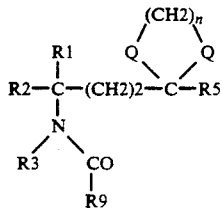
(V.D.3)

which are reduced with a metal hydride or organometallic hydride (Hm.2) defined above to a propanamine of formula (I.A.3) or of formula (I.D.3), and C.4 - for obtaining a propanamine (I) of formula (I.A.3) or of formula (I.D.3), in substituting the carbonitrile radical of an amino nitrile of formula (VII.1) or of formula (VII.2)

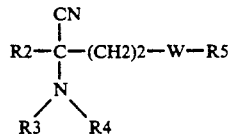
(VII.1)

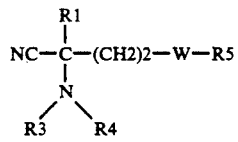
(VII.2)

in which W represents the groups defined for the propanamines (I) except for the group C=Q, R3 and R4 both being other than hydrogen, by the carbon-based radicals R1 or R2 of the organometallic reagents R1-M-X7 and R2-M-X8 in which:

R1 represents the radicals indicated for the propanamines (I) except when they are subsituted with halogen atoms, R2 represents a radical identical to those indicated for the propanamines (I), M is a divalent metal atom included in the group magnesium, cadmium and zinc, X7 and X8 are halogen atoms selected from chlorine, bromine or iodine, and for obtaining a propanamine of formula (I.D.3), in condensing a propanamine (I.C.3) with a bifonctionnal reagent HQ—(CH2)—QH in which Q is oxygen or sulfur and n has the value 2 or 3,

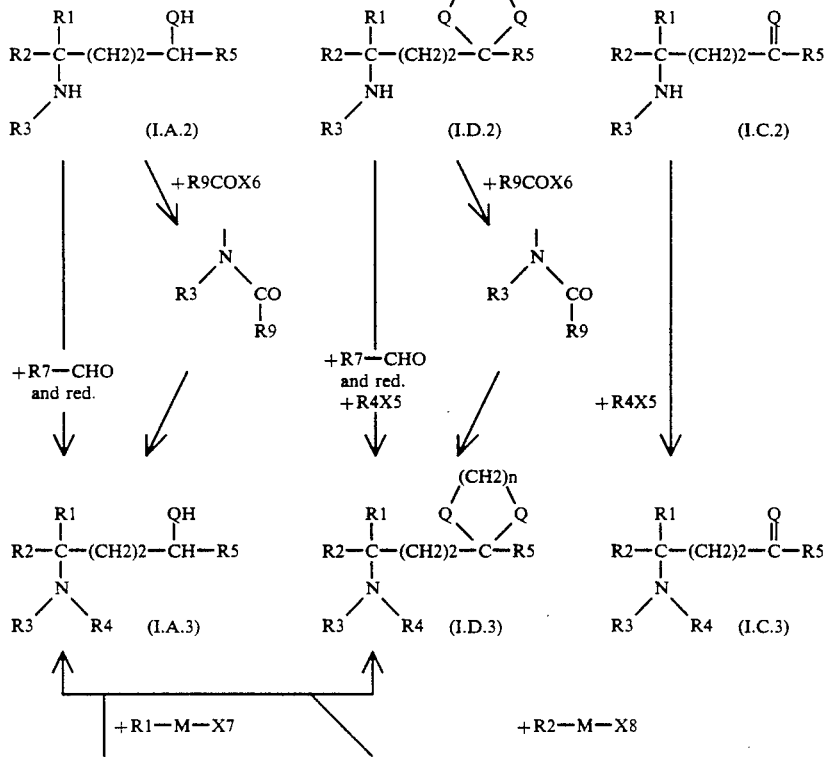

SCHEME 5

-continued

SCHEME 5

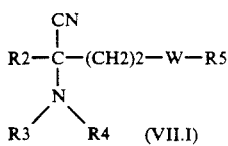 (VII.1)

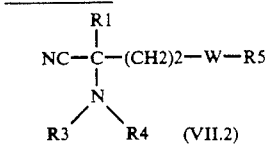 (VII.2)

C.5 —as is shown in Scheme 6, for preparing propanamines (I) in which R3 and R4 are not hydrogen,
and of formula (I.A.3), in reducing with a metal hydrigde or organometallic hydride (Hm.3) defined above a propanamine of formula (I.C.3)

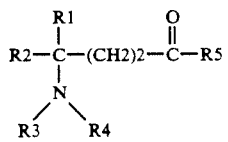 (I.C.3/O)

in oxidizing, with mono- or polyatomic ionic oxidation/reduction systems whose standard potential E° at 20° C. is greater than 0.60 V, a propanamine (I.A.3) in which the function QH is hydroxyl and of formula (I.A.3/O)

or in hydrolyzing with an acid solution or oxidizing solution a propanamine (I.D.3),
and of formula (I.C.3/S),

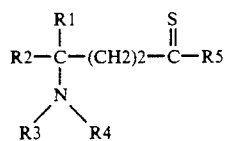 (I.C.3/S)

in reacting a propanamine (I.C.3/O) with a reagent Rz-NH2 described above, to obtain an intermediate (VI.2) of formula

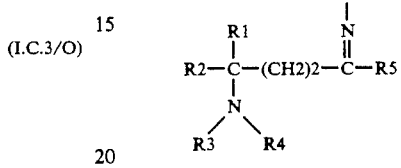 (VI.2)

which is employed in a thio-oxo substitution reaction with the above reagents

SCHEME 6

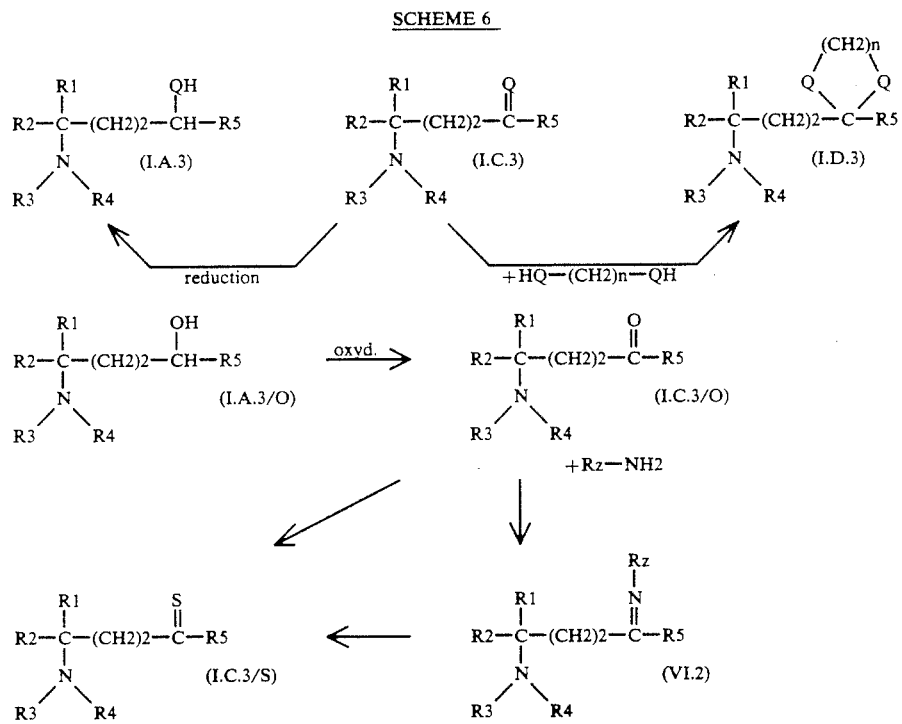

The invention elates, by way of intermediates, to the compound of formula (XX)

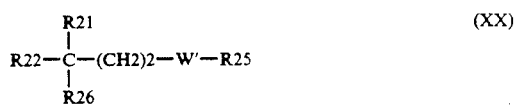 (XX)

in which:

R21 is a phenyl radical optionally mono, di or trisubstituted in an identical or different manner with halogen atoms or lower alkyl, lower haloalkyl or lower alkoxy radicals, or if a 5- or 6-membered monocyclic heteroaryl radical in which the single heteroatom is nitrogen, oxygen or sulfur, or is a carbonitrile radical when R22 is alkyl, R22 is a lower alkyl radical or is a carbonitrile radical when R21 is phenyl optionally substituted or heteroaryl, R25 is a 5- to 7-membered cycloalkyl radical, a phenyl radical or a 5- or 6-membered monocyclic heteroaryl radical in which the single heteroatom is nitrogen, oxygen or sulfur, which radicals are optionally mono-, di- or trisubstituted in an identical or different manner with halogen atoms or lower alkyl, lower haloalkyl or lower alkoxy radicals, R26 is a nitro radical when R21 or R22 are not carbonitrile, or when R21 or R22 is carbonitrile R26 is an amino group - N(R23)R24 in which R23 and R24 are a lower alkyl, lower alkenyl, lower cycloalkylalkyl, which may be identical or different without, however, both being lower cycloalkylalkyl, or, together with the nitrogen atom to which they are attached, form a saturated 5- to 6-membered heterocycle containing only one heteroatom, and W' represents a group =CH—QH or a heterocycle =C[Q—(CH2-)n—Q] when R21 or R22 are carbonitrile, or a group =C=Q when R26 represents a nitro group, and in which groups Q is an oxygen or sulfur atom, n has the value 2 or 3.

The invention also relates to a process for preparing the intermediates (XX) of formulae (II), (VII.1) and (VII.2), which consists:

for preparing a precursor (II), in alkylating a nitro derivative (VIII) of formula:

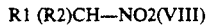

R1 (R2)CH—NO2(VIII)

with a reagent (IX.a) of formula:

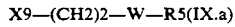

X9—(CH2)2—W—R5(IX.a)

in which X9 is a halogen atom such as chlorine or bromine or alternatively represents a function —N(R10)R11 in which R10 and R11 are lower alkyl, and are preferably methyl, and in which W represents a group =C=Q, for preparing a precursor (VII.1) or (VII.2), in alkylating an amino nitrile (X.1) or (X.2) of formula

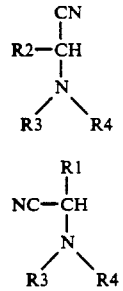

(X.1)

```
   CN
   |
R2—CH
   |
   N
  / \
 R3   R4
```

(X.2)

```
   R1
   |
NC—CH
   |
   N
  / \
 R3   R4
``` with a reagent (IX.b) of formula

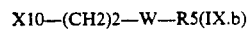

X10—(CH2)2—W—R5(IX.b)

in which X10 is a halogen atom such as chlorine, bromine or iodine or an arylsulfonyloxy or alkylsulfonyloxy radical, which is preferred, and W represents a group CH-QH or a heterocycle C[Q—(CH2)n—Q], which is preferred.

The compounds (VIII), (IX.a), (IX.b), (X.1) and (X.2) used for the synthesis of the propanamines (I) of the invention, are presented in the illustrative examples.

Explicitly, the process for preparing the compounds (II), (VII.1) or (VII.2) consists in preparing the anion of a compound (VIII), (X.1) or (X.2) and then in reacting it with a carbocation generated by an alkylating agent (IX.a) or (IX.b).

Thus, for an intermediate (VIII), the anion is favourably prepared in a lower alcohol comprising up to 4 carbon atoms, by reaction with an alkali metal alcoholate such as that of sodium or potassium, whereas, for a compound (X.1) or a compound (X.2), the preparation of the anion is carried out in an aprotic solvent such as 1,2-dimethoxyethane, THF or alternatively DMF, under the action of suitable bases derived from lithium amide such as lithium N,N-diethylamide or lithium N,N-diisopropylamide.

To illustrate these procedures, the alkylation of a compound (VIII) consists, for one mole of product employed, in first preparing the alcoholate needed for formation of the anion, which is carried out by adding 0.7 to 5 mole of alkali metal in 0.2 to 10 litres of appropriate lower alcohol, and then in first introducing the nitro derivative to prepare the corresponding anion therefrom and then adding an alkylating agent (IX.a). It is necessary, when, in this agent, X9 is lower dialkylamino, to add an excess of methyl iodide to prepare the corresponding quaternary ammonium derivative which generates the carbocation in the reaction medium itself.

In practice, the preparation of the alcoholate consists in adding with the requisite precautions, from 0.9 to 2.5 mole of sodium, which is the prefered alkali metal, in 0.25 to 1 litre of methanol or ethanol at a temperature below 20° C., and then, after formation of sodium alcoholate, and at a temperature below or in the region of 0° C., in adding an alcoholic solution of the compound (VIII). After formation of the anion, from 0.8 to 1.25 mole of alkylating agent (IX.a) are introduced in alcoholic solution, and then, if the agent is an N,N-dialkylamine, 1.2 to 1.9 mole of methyl iodide are also added. The reaction medium is maintained for 2 to 24 h at a temperature of between 10° and 60° C. in order to complete the alkylation, and then treated in a suitable manner to isolate and purify the intermediate compound (II) obtained.

And, to illustrate the alkylation of a compound (X.1) or (X.2) to a compound (VII.1) or (VII.2), a commercially obtained product or alternatively a compound prepared "in situ", which is the method used when employing lithium N,N-diisopropylamide, which is the preferred base for the preparation of anions with compounds (X.1) or (X.2), may be used for preparing the anion.

In this case, as a general example, the reaction is performed advantageously for one mole of compound with 0.5 to 3 litres of THF in which from 0.75 to 1.25 mole of lithium N,N-diisopropylamide has been prepared beforehand by mixing equimolecular and corresponding quantities of n-butyllithium and diisopropylamine at a temperature below −10° C.

The addition of the compound (X) and the formation of the anion are carried out at a temperature below 0° C., and preferably between −50° and −80° C., and in a period of 30 minutes to 5 hours. After this, from 1.0 to 1.5 moles of an alkylating agent (IX.b) are added at the same temperature and the latter is allowed to return to about 20° C. The reaction is then allowed to proceed for 1 to 24 hours before treatment according to the appropriate procedures for isolating and purifying the corresponding compound (VII.1) or (VII.2) thereby obtained.

To prepare the propanamines (I) of the invention, as has been described above, the process of the invention makes use of various reactions whose implementation is specified in that which follows and in the illustrative examples of the experimental part. Essentially these reactions are:

a) - reduction reactions carried out:

a.1) with metal hydrides or organometallic hydrides of general formula (Hm):

M1(t) M2 H(r) Rx(s)

in which

M1 is an alkali metal such as sodium or lithium,

M2 is an element of group III of the Periodic Classification such as boron or aluminum, (t) is equal to zero or one, (r) is the representative index of the number of hydrogen atoms and is equal to 1, 3 or 4, and Rx is a lower alkyl or alkoxy radical of which the index (s) is equal to 0, 1, 2 or 3, and these hydrides correspond to the equation: $r+s-t=3$.

The hydrides thus defined may be used in the form of complexes with organic compounds, such as the complexes of borane with tetrahydrofuran or dimethyl sulfide, or alternatively in combination with metal halides such as lithium chloride or aluminum chloride, and which make it possible a.1.1) to prepare propanamines (I) or their precursors in which W represents a group =CH—QH, by reduction of a corresponding compound in which W is a group =C=Q by means of a metal hydride or organometallic hydride as described above, and as is performed in order to obtain a compound (III) and to obtain a propanamine (I.A.3) from a propanamine (I.C.3).

The reduction of the groups C=Q is favourably carried out with hydrides in which M2 is boron, and among these preference is given to those in which M1 is sodium and the indices t and s have the value 1 and 0, respectively.

In this case, their use, taking sodium borohydride NaBH4 as an example, is carried out in water-miscible protic solvents such as lower alcohols, for example methanol or ethanol.

Thus, the reduction of one mole of compound is performed by dissolving it in 5 to 20 parts (weight/volume) of alcohol and then adding from 0.30 to 0.75 mole of NaBH4 to the solution without exceeding 30° C. The mixture is maintained for 1 to 5 hours at a temperature of between 15° C. and the refluxing temperature of the solvent, the complexes are then decomposed by adding water, acidified where appropriate, and the alcohol is removed by distillation. The reduction product is isolated and then purified by suitable methods such as crystallization, fractional distillation under high vacuum or alternatively preparative chromatography.

a.1.2) to prepare secondary amines —NH—R3 such as (I.A.2) and (I.D.2), or tertiary amines —N(R3)R4 such as (I.A.3) and (I.D.3), by reduction of corresponding carboxamide intermediates (V.A.2/3) or (V.D.2/3).

The hydrides used for this purpose correspond to the general formula defined, and more especially to those in which M2 is aluminum. Their use being carried out in anhydrous aprotic solvents such as ethers and aromatic solvents.

Among these, preference is given to hydrides which are soluble in aromatic hydrocarbons such as benzene or toluene, in which Rx, of which the index s is equal to 2, represents, in particular, a 2-methoxyethoxy radical; also by way of preference, aluminum hydride AlH3, which is prepared in the reduction medium by the reaction of three moles of lithium aluminum hydride with one mole of aluminum chloride, is used in ethers such as diethyl ether and THF.

The reduction of a carboxamide function requires from 3 to 6 mole of reducing agent at a temperature of between 0° C. and that of refluxing of the solvent.

However, under preferred conditions, 3.5 to 5 mole of reducing agent per mole of compound (V.A) or (V.D) are used, maintaining a temperature of between 0° and 25° C. when aluminum hydride is used, and the refluxing temperature of benzene or toluene when the organometallic hydride is used, the time, irrespective of the reducing agent, being between 1 and 6 hours, the state of progress being monitored, moreover, by periodic thin-layer chromatographic checks in order to stop the reaction at the opportune moment by a careful addition of water, which decomposes the complexes formed and the excess reagents. The usual treatments enable the products derived from the reduction to be isolated and then purified.

a.2) by hydrogenations catalyzed by metal elements of group VIII of the Periodic Classification of the elements, in their divided form or in their oxidized forms or their salified forms, it being possible for the dispersion of these various catalysts to be carried out on various inert supports such as, for example, activated charcoal, alumina or barium sulfate or carbonate.

Among the elements of group VIII, platinum, palladium or alternatively nickel, their salts and their oxides are preferred, and, in particular for nickel, the form of an alloy with aluminum in Raney nickel is preferred.

These hydrogenations make it possible to prepare, by reduction of nitro derivatives, propanamines (I) having a primary amine function such as (I.D.1) and (I.A.1) from the compounds (III) and (IV).

The implementation of the hydrogenation consists in dissolving the nitro derivative in 1 to 30 parts (w/v) of a lower aliphatic alcohol such as methanol or ethanol, then in adding the suitably prepared catalyst in the proportion of 10 to 100 g per mole of compound to be hydrogenated in the case of Raney nickel, and then in vigorously stirring the suspension under a hydrogen atmosphere at a pressure of between 10 and 50 bars and at a temperature of 20° to 60° C. until reduction of the derivative is complete, this being obtained when the absorption of hydrogen is complete, and which manifests itself, at a constant temperature and a constant volume, in a stabilisation of the pressure.

In most cases, under a hydrogen pressure of between 5 and 10 bars and at a temperature in the region of 25° C., the reaction is complete after 10 to 24 hours, after which the catalyst is filtered off, the alcohol evaporated off and the product derived from the hydrogenation is isolated and then purified by the usual methods. u b) - acylation reactions to prepare, as described above in B.2 intermediates (V.D.2) or (V.A.2), and in C.2.2 intermediates (V.D.3) or (V.A.3), which consist b.1) when the acylating reagent (R6-CO)pX2 is an anhydride (p=2; 2=0), the reaction, when the boiling point of the anhydride is below 140° C., may be performed without a solvent, in reacting a propanamine (I.A.1) or (I.D.1) in a large excess and at the refluxing temperature of the reagent. The preferred method consists, however, in carrying out the reaction using pyridine as a solvent and reacting from 1 to 5 mole of anhydride for one mole of compound to be acylated.

The use of 1.2 to 1.8 mole of anhydride under reflux of pyridine for 1 to 3 hours commonly leads to suitable results. The intermediates (V.A.2) or (V.D.2) obtained are, if their state requires it, purified by the usual methods, or employed as they are in the reduction reactions which follow in order to prepare the corresponding propamines as is described above in a.2).

b.2) when the acylating reagents (R6-CO)pX2 or R9COX6 are acyl halides (X2 or X6=Cl or Br), the propanamines (I.A.1), (I.D.1), (I.A.2) and (I.D.2) are solubilised in 3 to 20 volumes (w/v) of a halogenating apolar organic solvent such as dichloromethane, and an organic base such as triethylamine or any other strong organic base of comparable pk$_B$ and non-reactive is then added to the solution, followed by the acyl halide at a temperature of between $-20°$ C. and $+20°$ C., and more favourably between 0 and 15° C. The reaction medium is then maintained at about 20° C. for 1 to 24 h in order to complete the reaction, and thereafter diluted with water and treated in an appropriate manner, such as by extraction operations, to isolate and then purify the carboxamides (V) obtained, and b.3) when the reagent (R6-CO)pX2 or the reagent R9-COX6 are carboxylic acids (X2 or X6=OH), the acylation process consists in first preparing, in an ether such as THF, an equimolecular solution of the acid and an organic base such as N-methylmorpholine, and then adding thereto at a temperature of between $-50°$ and $0°$ C., and preferably between $-20°$ and $-10°$ C., a quantity equimolecular with respect to the above reagents of isobutyl chloroformate and then the propanamine to be acylated.

The reaction is allowed to proceed for 12 to 48 hours at a temperature of between 0° and 20 C. and the carboxamide (V) obtained is then isolated and purified, and b.4) more especially with formic acid, the acylation is carried out in the presence of 1,1'-carbonyldiimidazole in an anhydrous and a polar solvent such as THF.

In practice, to an equimolecular mixture of formic acid and 1,1'-carbonyldiimidazole, the propanamine to be treated is added at a temperature in the region of 0° C. in the proportion of 0.6 to 0.95 mole for 1 mole of formic acid. The mixture is maintained for 1 to 12 hours at a temperature of between 0° and 20° C. in order to complete the reaction, then treated in the usual manner to isolate and purify the carboxamide (V) obtained, and c) - condensation reactions which consist, for example for preparing an intermediate (IV) from a precursor (II) or alternatively a propanamine (I.D.3) from a propanamine (I.C. 3), in reacting a bifunctional reagent HQ-(CH2)n—QH with a compound in which W represents =C=Q.

By way of example, to obtain a heterocycle W which is a 1,3-dioxolane-2,2-diyl group from a compound in which W is =C=Q in which Q is oxygen, various techniques may be used, such as those described in the chapter "Protection for The Carbonyl Group" in "Protective Groups in Organic Synthesis" T. W. Greene Ed. Wiley 1981, p. 115-151. A preferred procedure consists in dissolving the carbonyl derivative in 3 to 50 volumes (w/v), and commonly in 5 to 20 volumes, of an aromatic organic solvent which is inert with respect to the reagents employed and capable of entraining water by azeotropic distillation in order to remove it after condensation of the distillate, such as benzene or toluene, and then adding from 2 to 40 moles of ethylene glycol and a catalyst which is selected from strong inorganic or organic acids such as hydrochloric, sulfuric, methanesulfonic or p-toluenesulfonic acids. The mixture is brought to the refluxing temperature of the azeotrope from which, after condensation, the water formed is removed in continuous fashion during the reaction by a system such as that of Dean and Stark. The completion of removal of water is characteristic of the end of the reaction, which necessitates from 30 minutes to 24 hours of refluxing.

Under usual conditions, the condensation is performed by adding from 3 to 10 mole of ethylene glycol and from 2 to 10 ml of concentrated sulfuric acid (d=1.84) for one mole of carbonyl compound. The reaction is complete after 10 to 16 hours of refluxing, after which the compound derived from the condensation is isolated and purified.

d) - hydrolyzis reactions for obtaining propanamines (I.C) in which W is a carbonyl group (Q=oxygen) from propanamines (I.D) in which W is a heterocycle, for preparing a propanamine (I.C. 2/0) from a propanamine (I.D.2) or for preparing a propanamine (I.C. 3/0) from a propanamine (I.D.3).

The process used can consist in the application of a method described, for example, in "Protection for the Carbonyl Group" (reference already cited), and which consists, when in the heterocycle Q represents oxygen, in performing a hydrolyzis in solution in a lower alcohol or in an aqueous-alcoholic mixture with a strong inorganic or organic acid, and when Q is sulfur, in performing this hydrolyzis with an oxidizing solution such as those of water-soluble mercury (II), silver (I) or copper (II) salts or alternatively with oxidizing organic compounds such as chloramine B or T.

As a general illustration, the preferred method for hydrolyzing a 1,3-dioxolane-2,2-diyl group consists in dissolving the compound to be hydrolyzed in a water-miscible organic solvent selected, for example, from the group comprising lower aliphatic ketones, in adding thereto an aqueous solution of a strong acid, preferably hydrochloric acid, and in bringing the mixture to reflux until the hydrolyzis reaction is complete, which may be determined by thin-layer chromatographic checks carried out periodically during the reaction. Specifically, one mole of compound to be treated is solubilised in 3 to 5 litres of acetone, an equivalent volume of an approximately N solution of hydrochloric acid is then added and the mixture is brought to reflux for 30 minutes to 5 hours, the progress of the hydrolyzis being monitored by TLC., the acetone is then removed by distillation and the residue treated in a suitable manner to isolate and purify the propanamine (I) in which W is carbonyl.

e) - alkylation reactions e.1) with alkyl halides, which consist:

e.1.1. in a monoalkylation with a reagent R3-XI for preparing propanamines (I.A.2) or (I.D.2) and with a reagent R4-X5 for preparing propanamines (I.D.3) and (I.C. 3).

The reaction is carried out under conditions suited to favouring the monoalkylation of the amine, this being carried out in the solvents which are inert with respect to the reagents, such as, for example, toluene and acetonitrile, and by reacting one mole of propanamine with 0.5 to 6.0 mole of halide R3-XI or R4-X5.

Preferably, from 0.8 to 1.2 mole of derivative in which the halogen is bromine or iodine is used, and an organic or inorganic base is optionally added to favour the reaction, which consists in heating the reaction medium to a temperature of between 20° and 110° C. for 2 to 5 h, the products then being isolated and purified by the usual methods, in particular by chromatography.

e.1.2 in a dialkylation of a propanamine (I.D.1) with a dihalide X3-(CH2)q-X4, which consists in carrying out the reaction as described above, but preferably using from 1.2 to 2.0 mole of halogenated derivative and carrying out the reaction at a temperature of between 60° and 110° C. for 4 to 24 hours to obtain an N-heterocyclic propanamine (I.D.3).

e.2) with aldehydes R7-CHO and reducing agents, and which consist e.2.1 in a dialkylation to obtain, from propanamines (I.A.1) or (I.D.1), propanamines (I.A.3) or (I.D.3) in which R3 and R4 are identical, and which is carried out by reacting the propanamine to be treated with from 2 to 5 mole, and more favourably from 2.2 to 3 mole, of aldehyde and then in reacting a reducing agent which can be either formic acid or one of its salts according to the Eischweiler-Clarke reaction (J. Am. Chem. Soc. 55, 4571, 1933), or alternatively a hydride of a metal of group III of the Periodic Classification of the elements, such as boron, and more especially among these sodium cyanoborohydride NaBH3CN, using an adaptation of the method in J. Med. Chem. 25, No. 4, 446, (1982).

As an example of an N,N-dimethylation of a propanamine (I.A.1) or (I.D.1) by the Eischweiler-Clarke reaction, one mole of amine is initially mixed intimately with 2 to 5 mole, and more favourably 2.2 to 3.0 mole, of approximately 37% (w/v) aqueous formaldehyde solution, 2 to 6 moles of pure formic acid, and preferably from 2.5 to 3.3 mole, are then introduced at between 0° and 10° C., and the mixture is gradually heated to 100° C until the gaseous evolution has ceased, which requires from 15 minutes to 4 hours and more frequently from 45 minutes to 2 hours.

The mixture is then treated, in particular, by extractions to isolate the propanamine (I.A.3) or (I.D.3), which is purified by the usual methods.

e.2.2 in a monoalkylation for preparing a propanamine (I.A.3) or (I.D.3) by reductive alkylation of a corresponding propanamine (I.A.2) or (I.D.2), and which consists in performing a reaction such as one of those described above using, however, one half the quantity of the reagents indicated.

f) - substitution reactions of carbonitrile radicals of precursors (VII.1) or (VII.2) with radicals R1 or R2 belonging to halometallic reagents for preparing propanamines (I.D.3) or (I.A.3).

It is preferable to work according to a reaction described by N. J. Leonard et al., J. Am. Chem. Soc., 1956, 78, p. 1986 and 1957, 79, p. 5279, in which substitution of the carbonitrile radical of the compound (VII.1) or (VII.2) by a radical R1 or R2 is carried out using an organomagnesium derivative in ethers such as diethyl ether, methyl t-butyl ether, diisopropyl or dibutyl ethers or alternatively tetrahydrofuran, which is the preferred solvent, and consists in reacting 1.5 to 6 mole of organomagnesium derivative for one mole of precursor at a temperature of between 5° and 50° C. for 30 minutes to 12 hours.

The preferred method consists in adding, at a temperature of between 10° and 20° C., 1 mole of precursor (VII.1) or (VII.2) dissolved in THF to 4 to 5 mole of the organomagnesium compound also dissolved in THF. The reaction is continued for 2 to 5 hours at the same temperature and the complex obtained is then decomposed by adding aqueous ammonium chloride solution. After treatment, the propanamine (I.D.3) or (I.A.3) obtained is isolated and purified by the methods already mentioned.

g) - oxidation reactions, for obtaining a propanamine in which W is a carbonyl =C=O from corresponding propanamines in which W is hydroxymethylene =CH—OH, such as for obtaining (I.C. 2/0) from a hydroxylated propanamine (I.A.2) or for obtaining (I.C. 3/0) from a hydroxylated derivative (I.A.3).

The reaction may be carried out using various reagents capable of oxidizing a secondary alcohol function to a ketone function, and which are summarised, for example, in "Advanced Organic Chemistry"- J. March - 3rd Ed. Wiley, p. 1057–1060. Mono- or polyatomic ionic oxidation/reduction systems whose standard potential E at 20 C. is greater than 0.60 volts are used for these reactions.

And, more especially, polyatomic ions derived from oxidation of chromium, manganese or nitrogen, whose potential E° is in the region of or greater than 1 volt, such as the permanganate ion MnO4- or dichromate ion Cr2O7—, which is preferred and which is obtained from potassium or sodium dichromate in the presence of sulfuric acid, are used.

The oxidation reaction commonly performed consists in preparing a solution containing from 0.3 to 0.5 mole of dichromate with 0.6 to 1.0 mole of sulfuric acid and then adding 0.6 mole of hydroxy-propanamine to be oxidized thereto. The temperature is maintained at between 40° and 60° C. for 2 to 6 hours and the mixture is then treated, in particular by extraction in an alkaline medium, to obtain the compound resulting from the oxidation, which is isolated and purified by the usual methods.

h) - sulfuration reactions for obtaining propanamines c (I) in which W represents a C=S group from corresponding propanamines (I) in which W represents a C=O group, as, for example, for obtaining a compound (I.C. 2/S) or a compound (I.C. 3/S).

Preference is given to the reaction which consists in preparing initially an intermediate with a reagent Rz—NH2 in which, more especially, Rz is Rz'—NH— in which Rz' is hydrogen, lower alkyl or phenyl, to obtain a corresponding intermediate hydrazone (VI.1) or (VI.2) which, dissolved in benzene, is treated with sulfur monochloride to obtain a propanamine (I.C. 2/S) or alternatively (I.C. 3/S) shown above.

The implementation of these reactions is illustrated without implied limitation by the description in the experimental part of the products (I) of the invention and their intermediates.

Except where specially stated, in these examples, the isolation and purification procedures employ the usual methods such as crystallization, fractional distillation (in particular under high vacuum) and methods of preparative chromatography such as the technique of rapid chromatography performed on silica gel (Merck product ref. 4063) according to Still W. C. et al., J. Org. Chem. 43, 2923, 1978 or the technique of chromatography on a silica column obtained after axial compression with a Jobin-Yvon brand apparatus.

The determinations of purity and identity of the products are performed by the usual methods, which are recorded briefly:

determination of the melting point by the capillary tube method, the value of which obtained is uncorrected, determination of purity by thin-layer chromatography on silica 60 F 254, 0.25 mm thick (Merck product Ref. 5714), the chromatograms being examined after development under ultraviolet light at 254 nm and/or after spraying with Dragendorff's reagent or toluidine reagent, determination of identity by:

i) proton nuclear magnetic resonance spectrum, produced with a JEOL FX-90 P apparatus (90 MHz), tetramethylsilane (TMS) being used as internal reference; the spectra of the compounds being described, in the examples, by the chemical shift of the signals (in p.p.m. relative to TMS), their multiplicity, their integration, and, where appropriate, their exchange after addition of deuterium oxide being noted, and ii) infrared spectrography of the compounds in KBr disks or in films or alternatively in solution in CCl4 or alternatively in suspension in Nujol (R), on a Schimadzu IR-435 apparatus. The largest and most characteristic absorptions are recorded in the examples as the wavelength in cm-1.

Elemental analyses, in particular those of the compounds (I) were performed. Other than in exceptional cases (solvates, for example), the results thereof, in agreement with accepted standards, are not recorded; however, the elements analysed are mentioned. Finally, abbreviations commonly used (for example THF for tetrahydrofuran) may be employed in the description of these examples.

As regards TLC, the elution solvents used are indicated in the part describing the compounds of the invention by their initial letter S.(solvent) indicating the mixtures shown below and in which the proportions shown are in v/v.

| | |
|---|---|
| E.1 - ethyl acetate | |
| E.2 - ethyl acetate/ethanol | 3:1 |
| B. - benzene/ethanol | 85:15 |
| M.1 - methylene chloride | |
| M.2 - methylene chloride/methanol | 19:1 |
| H.1 - hexane/ethyl acetate | 1:1 |
| H.2 - hexane/ethyl acetate | 1.5:1 |
| H.3 - hexane/ethyl acetate | 2:1 |
| H.4 - hexane/ethyl acetate | 3:1 |
| H.5 - hexane/ethyl acetate | 4:1 |
| H.6 - hexane/ethyl acetate | 6:1 |
| H.7 - hexane/methylene chloride | 7:3 |

PREPARATION OF THE INTERMEDIATE COMPOUNDS

INTERMEDIATES IX

—IX.a: X9=(CH3)2N—; W=CO

Intermediate IX.a.1 3-dimethylamino-1-(3,4,5-trimethoxyphenyl)-propan-1-one.

IX.a; X9=(CH3)2N—, W=CO, R5=3,4,5(CH3O)3-C6H2]

55 ml of ethanol 9.3 g (0.31 mol) of paraformaldehyde, 50.0 g (0.24 mol) of 3,4,5-trimethoxyacetophenone, 25.2 g (0.31 mol) of dimethylamine hydrochloride and 1.0 ml of concentrated hydrochloric acid (d = 1.18) are introduced into a reactor. The mixture is heated and brought to reflux for two hours and then, after cooling, 400 ml of acetone are added and the mixture is again heated to reflux for 25 minutes.

The mixture is then cooled and kept for two hours in an ice-chest.

The crystallized hydrochloride is filtered off and then dried under vacuum.

Weight=41.0 g; Yld.=57%; M.p. 175° C.;

To obtain the product in the form of a base, the above compound is treated with a mixture of saturated sodium carbonate solution and dichloromethane. The organic phase is separated and the aqueous phase then reextracted with dichloromethane. The combined organic phases are washed with water and then dried over Na2SO4.

The concentrated solution enables an oily residual orange-colored product (34.2 g) to be obtained, which product is purified by recrystallization in hexane.

Weight=31.0 g; Yld.=49%; M.p. 47° C.;

Intermediate IX.a.2: 3-dimethylamino-1-(3,4-dichlorophenyl)- o propan-1-one.

[IX.a: X9=(CH3)2N—, W=CO, R5=3,4(Cl)2-C6H3]

According to a process identical to the above example and starting with 3,4-dichloroacetophenone, the product is obtained and purified by crystallization. M.p.51° C.

Intermediate IX.b.1: 2-methylsulfonyloxvethyl-2-phenyl-1,3dioxolane.

[IX.b: X10=CH3—SO3—, W=C(OCH2CH2O), R5=C6H5]

i) A mixture of 185.6 g (0.97 mol) of ethyl β-oxobenzenepropanoate, 350 ml (6.3 mol) of ethylene glycol and 1.9 ml of concentrated sulfuric acid (d=1.88) in 1.1 l of benzene is brought to reflux with stirring, the water formed being removed by a Dean and Stark separating system.

After 24 hours, a further 2.0 ml of acid are added and the mixture is brought to reflux for a further 22 hours. The mixture is cooled and dilute sodium bicarbonate solution is added. The organic phase is separated, washed with water, dried over Na2SO4 and then concentrated under vacuum. An oily residue of ethyl 2-ethyloxycarbonylmethyl-2-phenyl-1,3-dioxolane is obtained.

Weight=199.0 g; Yld.=87%;

ii) 16.04 g (0.425 mol) of lithium aluminum hydride in 600 ml of ether dehydrated over a molecular sieve are introduced into an anhydrous reactor under a nitrogen atmosphere. 98.1 g (0.415 mol) of the above ester i), dissolved in 20 ml of ether, are then added over a period of approximately 30 minutes. The mixture is stirred for 30 minutes at room temperature and then three hours under reflux, after which it is cooled and 25.5 ml of 10% w/v sodium hydroxide solution are added dropwise thereto. 250 ml of ether and 32 ml of water are then added, and the mixture, after stirring for 16 hours, is then filtered and concentrated under vacuum to obtain crude 2-hydroxyethyl2-phenyl-1,3-dioxolane in the form of a colorless oil.

Weight=73.7 g Yld.=91%, iii) 15.6 g (80 mmol) of the derivative prepared in stage ii) above and 17.0 ml of triethylamine are introduced into 250 ml of anhydrous dichloromethane. 6.85 ml (88.5 mmo]) of methanesulfonyl chloride are added dropwise under a nitrogen atmosphere and at −10° C. After stirring for 15 minutes at the same temperature, the mixture is extracted successively with water, dilute sodium bicarbonate solution and hydrochloric acid solution and is then finally dehydrated over Na2SO4. The solvent is removed by distillation under vacuum and the residue is crystallized in a hexanes/ethyl acetate mixture. After filtration and drying, 20.6 g of product are obtained.

Yld.=94%; M.p. 50° C.
TLC: 0.35-0.40; S. H.3

Intermediate IX.b.2: 2-methylsulfonyloxyethyl-2-(3,4,5-trimethoxyphenyl-1,3-dioxolane.

[IX.b; X10 =CH3—S03—, W=C(OCH2CH20), R5=3,4,5(CH30)3-C6H2]

The compound is prepared as described in the above procedure IX.b.1, from methyl 3,4,5-trimethoxyoxobenzenepropanoate (prepared according to R. E. Strube "Org. Synthesis", et al., vol. IV, Wiley, New York, 1963, p. 417) and the following compounds being obtained successively:

i) 2-acetyloxyethyl-2-(3,4,5-trimethoxyphenyl)-1,3dioxolane.

Yld.=78%; M.p. 76° C. (hexanes); TLC: 0.30; S. H.2 ii) 2-hydroxyethyl-2-(3,4,5-trimethoxyphenyl)-1,3-dioxolane.

Yld.=65%; M.p. 68° C. (hexanes); TLC: 0.30; S. H.1 iii) Intermediate compound IX.b.2

Yld.=57%; M.p. 94° C. (hexanes); TLC: 0.45; S. H.1

Intermediate IX.b.3:2-bromoethyl-2-cyclohexyl-1,3-dioxolane.

[IX.b : X10=Br, W=C(OCH2CH20), R5=CH(CH2)5]

2-methylsulfonyloxyethyl-2-cyclohexyl-1,3-dioxolane is prepared according to the process described for the compounds IX.b. 19.5 g (70 mmol) of the product are mixed with 45.1 g (140 mmol) of tetrabutylammonium bromide and 15.0 ml (140 mmol) of 2,2'-dimethyl-1,3-dioxolane in 250 ml of 1-bromopropane. The mixture is brought to reflux for 14 hours, then cooled and concentrated under vacuum, and the residue is treated with water, ether and hexanes. The aqueous phase is separated after settling has taken place and extracted again with a hexanes/ether mixture. The organic phases are combined, washed with water and saturated with sodium bicarbonate and then dried over Na2SO4. The solvent is removed and the compound is obtained in the form of a colorless liquid. Weight=17.9 g; Yld.=97%.

INTERMEDIATES VIII

General procedure:

i.1) 50 ml of ether dehydrated over a molecular sieve and then 1.9 g (50 mmol) of lithium aluminum hydride are introduced into a reactor under a nitrogen atmosphere. The suspension is cooled to about 5° C. and 100 mmol of a ketone R1 CO-R2, dissolved in 50 ml of ether, are then added in the course of approximately 30 minutes and at a temperature of between 0° and 5° C. The suspension is maintained for 30 minutes at room temperature and 30 ml of 10% (w/v) sodium hydroxide solution is then cautiously added followed by 10 ml of water. The insoluble matter is filtered off and the filtrate evaporated. The residual crude alcohol R1 -CHOH-R2 is purified by distillation unde high vacuum.

i.2) Or alternatively, 50 ml (100 mmol) of a solution of an organomagnesium derivative R2-MgBr in tetrahydrofuran are introduced into an anhydrous reactor under a nitrogen atmosphere. After cooling to a temperature of between 0 and 5° C., 100 mmol of aldehyde R1 —CHO, dissolved in 30 ml of tetrahydrofuran, are introduced in the course of one hour and at a temperature below 10° C. The mixture is stirred for 30 minutes and then precipitated in 125 ml of ice-cold water. 75 ml of 15% (w/w) sulfuric acid solution are then added to dissolve the precipitate, and the mixture is thereafter extracted with ether. The organic phases are washed, dried over Na2SO4 and then concentrated under vacuum. The alcohol R1 —CHOH—R2 is purified by distillation under high vacuum.

ii) 50 ml of toluene and 100 mmol of alcohol R1 —CHOH—R2 are introduced into a suitable reactor. 36 mmol of phosphorus tribromide are then added in the course of approximately 30 minutes and without exceeding 35° C.

The mixture is heated to reflux for 45 minutes and then cooled. The toluene phase is washed with saturated sodium bicarbonate solution and then with saturated NaCl solution and finally dried over Na2SO4. The solvents are evaporated off under vacuum and the residual brominated residue R1—CH(Br)—R2 is purified by distillation under high vacuum.

iii) 200 mmol of sodium nitrite are added to 75 ml of dimethyl sulfoxide in a reactor. The mixture is stirred and 100 mmol of bromo derivative prepared in ii) are added without exceeding 10° C.

The mixture is stirred for 2 hours 30 minutes and then precipitated in 200 ml of ice-cold water; it is then extracted several times with hexane.

The combined organic phases are dried over Na2SO4 and the solvent is then removed by distillation under vacuum. The nitro derivative R1 —CH(NO2)-R2 is purified by distillation under high vacuum with precaution against hard and sudden decomposition.

The intermediate compounds VIII.1 to VIII.5 described below are prepared according to this protocol.

Intermediate VIII.1: 1-nitro-propylbenzene.

[VIII: R1=C6H5, R2=C2H5]

Prepared from 1-phenyl-1-propan-1-ol ii) 1-bromo-propylbenzene: Yld.=90%; B.p. 101°-110° C./2600Pa, iii) 1-nitro-propylbenzene: Yld. 66%; B.p. 68°-78° C./65Pa Intermediate VIII.2: 1-(4-chlorophenyl)-1-nitro-propane

[VIII : R1=p.Cl-C6H4, R2=C2H5]

Prepared from p-chloropropiophenone.

i.1) 1-(4-chlorophenyl)-propan-1-ol
Yld. =82%; B.p. 92° C./65Pa ii) 1-(4-chlorophenyl)-1-bromo-propane
Yld.=81%; B.p. 70° C./20Pa, iii) 1-(4-chlorophenyl)-1-nitro-propane
Yld.=50%; B.p. 95°-115° C./40Pa; TLC: 0.85 ; S. M.1 , Intermediate VIII.3: 1-(4-methylphenyl)-1-nitro-propane

[VIII: R1=p.CH3-C6H4, R2=C2H5]

Prepared from 4-methylpropiophenone.
Yld. =91%, B.p. 70°-85° C./7Pa, ii) 1-(4-methylphenyl)-1-bromo-propane
Yld. =90%; B.p. 60°-65 C./13Pa iii) 1-(4-methylphenyl)-1-nitro-propane
Yld.=62%; B.p. 76°-81° C./25Pa; TLC: 0.80 ; S. M.1.

Intermediate VIII.4: 1-(4-trifluoromethylohenyl)-1-nitroane.

[VIII; R1=p.F3C-C6H4, R2=C2H5]

Prepared from 4-trifluoromethylbenzaldehyde.

i) 2) 1-(4-trifluoromethylphenyl)-propan-1-ol
Yld.=92%; B.p. 60°-65° C./60Pa, ii) 1-(4-trifluoromethylphenyl)-1-bromo-propane Yld.=69%; B.p. 57°-70° C./130Pa, iii) 1-(4-trifluoromethylphenyl)-1-nitro-propane
Yld.=45%; (chromatography); TLC: 0.50; S. H.7

Intermediate VIII.5: 1-(3,4-dichlorophenyl)-1-nitro-propane.

[VIII; R1=3,4(Cl)2-C6H4, R2=C2H5]
Prepared from 3,4-dichlorobenzaldehyde.

i.2) 1-(3,4-dichlorophenyl)-propan-1-ol
Yld.=93%; B.p. 110° C./25Pa.

ii) 1-(3,4-dichlorophenyl)-1-bromo-propane
Yld.=89% B.p. 88°-98° C./25Pa.

iii) 1-(3,4-dichlorophenyl)-1-nitro-propane
Yld.=55% (chromatography); TLC: 0.90; S. M.1,

INTERMEDIATE X

Intermediate X.2 : α-(dimethylamino)-phenylacetonitrile.

[R1=C6H5, R3=R4=CH3]

A solution of 20.3 ml (200 mmol) of benzaldehyde in 20 ml of methanol is added dropwise to a solution of 11.8 g (240 mmol) of sodium cyanide and 19.6 g (240 mmol) of dimethylamine hydrochloride in 40 ml of water and over a period of 75 minutes at a temperature of 30° to 40° C. Stirring is continued for 4 hours at 30° C.; 150 ml of water are added and the mixture is extracted with 4 times 200 ml of ether, the combined ether phases are washed with water, then with 25% (w/v) of sodium bisulfite solution and washed again with water. After drying over Na2SO4, the ether is removed by distillation and the residue purified by fractional distillation.

Weight=30.4 g; Yld.=95%, B.p. 75° C./100Pa.

INTERMEDIATES VII

General procedure: In a reactor protected from moisture and maintained under a nitrogen atmosphere, 100 mmol of n-butyllithium, in 2M solution in hexane, are introduced dropwise at −10° C. into a solution of 105 mmol of diisopropylamine propylamine in 100 ml of tetrahydrofuran. The solution is maintained for 15 minutes at −10° C. It is cooled to −78° C. and 100 mmol of amino nitrile intermediate (X), dissolved in 100 ml of THF, are introduced dropwise and in the course of 15 minutes at −78° C. The solution is then stirred for 2 hours at this temperature, thereafter 105 mmol of intermediate IX.b [X10=halogen, W=C(O—CH2—CH2) are added, and the mixture is left stirring for 15 minutes at −78° C. and then an hour and a half at room temperature. 300 ml of 10% (w/v) ammonium chloride solution are then added and the mixture is extracted with ether.

The combined ether phases are washed and dried over Na2SO4. The ether is evaporated off and the crude residual product, the purity of which is assessed by TLC, is used without further treatment in the reaction which follows.

The compounds (VII). 2a, b and c are prepared according to this protocol by reaction of the intermediate (X) with the alkylating agents described under the intermediates (IX.b).

Intermediate VII.2.a:2-(1-cyano-1-N,N-dimethylamino-1-phenylprop-3-yl)-2-phenyl-1.3-dioxolane.

[VII.2; R1=R5=C6H5, R3=R4=CH3]
Prepared from the intermediates X.2 and IX.b.1
Yld.=84%; TLC: 0.50; S. H.1, Intermediate VII.2b: 2-(1-cyano-1-N,N-dimethylamino-1-phenylprop-3-yl)-2-(3,4,5-trimethoxyphenyl)-1.3-dioxolane.

[VII.2; R1=C6H5, R3=R4=CH3, R5=(CH3O)3-C6H2]
Prepared from the intermediates X.2 and IX.b.2
Yld.=57%; TLC: 0.60; S. H. 3, Intermediate VII.2c: 2-(1-cyano-1-N,N-dimethylamino-1-phenylprop3-yl)-2-cyclohexyl-1-dioxolane.

[VII.2; R1=C6H5, R3=R4=CH3, R5=CH(CH2)5]
Prepared from the intermediates X.2 and IX.b.3
Yld.=74%; TLC: 0.20; S. H.6.

INTERMEDIATES (II)

General procedure: 4.83 g (209 mmol) of sodium are added to 80 ml of methanol in an anhydrous reactor under a nitrogen atmosphere. The temperature of the medium rises to 70° C. After dissolution, the mixture is cooled to 0° C. and a solution of 100 mmol of a nitro intermediate (VIII), dissolved in 20 ml of methanol, is then introduced dropwise in the course of approximately 15 minutes. Stirring is maintained for 15 minutes and 100 mmol of a ketone (IX.a), dissolved in 50 ml of methanol, are then introduced.

The mixture is stirred for 15 minutes and 10.05 ml (160 mmol) of methyl iodide are then added thereto. The mixture is again stirred for 30 minutes at 0° C. and then overnight at room temperature.

The precipitate is filtered off and recrystallized in isopropanol for purification.

The intermediates II.a to II.g described below are prepared according to this procedure applied to the intermediates (VIII) and (IX.a) described above.

Intermediate II.a: 1-(3,4-dichlorophenyl)-4-nitro-4-phenylhexane-1-one.

[II; R1=C6H5, R2=C2H5, R5=3,4(Cl)2-C6H3]
Prepared from VIII.1 and IX.a.2
Yld.=57%; M.p. 130° C.(hexanes/ethyl acet.),
TLC: 0.50; S. H.4

Intermediate II.b: 1,4-diohenyl-4-nitro-hexan-1-one.
[II; R1=R5=C6H5, R2=C2H5]
Prepared from VIII.1 and 3-(dimethylamino)propiophenone hydrochloride.
Yld.=65%; M.p. 96° C.(hexanes/ethyl acet.).
TLC: 0.40; S. H.3

Intermediate II.c : 4-nitro-4-phenyl-1-(3.4,5-trimethoxyphenyl)hexan-1-one.
[II; R1=C6H5, R2=C2H5, R5=3,4,5(CH3O)3-C6H2]
Prepared from VIII.1 and IX.a.1
Yld.=47%; M.p. 86° C. (methanol),
TLC: 0.50; S. H.3

Intermediate II.d: 4-(4-chlorophenyl)-4-nitro-1-(3,4,5trimethoxyphenyl)-hexan-1-one.
[II; R1=p.Cl-C6H4, R2=C2H5, R5=3,4,5(CH3O)3-C6H2]
Prepared from VIII.2 and IX.a.1
Yld.=67%; M.p. 80° C.(isopropanol),
TLC: 0.30; S. M.1

Intermediate II.e: 4-nitro-4-(4-methylphenyl)-1-(3,4,5-tri-methoxyphenyl)-hexan-1-one.
[II R1=p.CH3-C6H4, R2=C2H5, R5=3,4,5(CH3O)3-C6H2]
Prepared from VIII.3 and IX.a.1
Yld.=61%, M.p. 63° C.(isopropanol),
TLC: 0.25; S. M.1

Intermediate II.f: 4-nitro-4-(4-trifluoromethylohenyl)-1-(3,4,5-trimethoxyphenyl)-hexan-1-one
[II; R1=p.F3C-C6H4, R2=C2H5, R5=3,4,5(CH3O)3-C6H2]

Prepared from VIII.4 and IX.a.1
Yld.=82%; M.p. 130° C.(isopropanol),

TLC: 0.40; S. M.1

Intermediate II.g: 4-(3,4-dichloroohenyl)-4-nitro-1-(3,4,5-trimethoxyphenyl)-hexan-1-one.
[II; R1=3,4(C1)2-C6H3, R2=C2H5, R5=3,4,5(CH3O)3-C6H2]
Prepared from VIII.5 and IX.a.1
Yld.=77%; M.p. 127° C.(isopropanol).
TLC: 0.30; S. M.1

PREPARATION OF THE COMPOUNDS OF THE INVENTION:EXAMPLES

EXAMPLES 1

General procedure:

stage a (preparation of the intermediate nitrodioxolane IV from nitro ketone II).

100 mmol of a nitro ketone II, 350 ml of benzene and 34 ml (450 mmol) of ethylene glycol are introduced into a reactor equipped with a stirring system and a condenser in the reflux position provided with a water separation system of the Dean Stark type. The heterogenous mixture is stirred, 0.7 ml of concentrated sulfuric acid (95/97%; d=1.84) is added thereto and the mixture is then heated and kept refluxing for 16 hours with stirring in order to remove the water formed by the reaction as it forms.

After being cooled to room temperature, the mixture is precipitated in 300 ml of saturated sodium bicarbonate solution. The aqueous phase is separated and extracted with twice 150 ml of ether. The combined organic phases are washed with water and dehydrated over Na2SO4. The solvents are removed by distillation under reduced pressure and the residue is purified, if necessary, by a suitable method.

stage b (compound of the invention I.D.1 from intermediates IV).

100 mmol of a nitrodioxolane intermediate IV and 350 ml of ethanol are introduced into a leakproof reactor tested to a pressure of approximately 12 bars and equipped with a vigorous stirring system. 7.0+/−1.0 g of activated Raney nickel (type W 2), suspended in approximately 50 ml of ethanol, are added under a nitrogen atmosphere.

The reactor is hermetically sealed and a succession of purges is then carried out, consisting in introducing alternately, three times and without stirring, nitrogen and then hydrogen under a pressure of approximately 5 bars. When this procedure is complete, hydrogen is introduced under a pressure of 8 bars and the suspension is stirred with extreme vigour for 16 hours, after which period the internal pressure is stable and the hydrogenation is complete.

The catalyst is filtered off on a Buchner lined with a bed of infusorial earth and the filtrate is concentrated under reduced pressure.

The residue is purified, where appropriate, by the usual methods, excluding, however, aqueous treatments in an acid or alkaline medium.

The compounds I.D.1 of the invention of Examples 1.a to 1.g are prepared according to this protocol from the nitro ketones II.a to II.g described above.

Example 1.a: 2-(3-amino-3-phenyl-pentan-1-yl)-24-dichlorophenyl)-1,3-dioxolane.
[I; R1=C6H5, R2=C2H5, R3=R4=H, R5=3,4(Cl)2-C6H3, W=C(O—CH2—CH2—O)]

a) Prepared from the nitro ketone II.a, the crude product (Yld.=75%) is employed without further treatment in the next stage.
b) Yld.=73% crude (oil); M.p. 63° C. (hexanes)
TLC: 0.60–0.80; S. H.3
NMR: 0.60 (t,3H), 1.25–1.95 (m,8H), 3.55–4.05 (m,4H), 7.10–7.50 (m,8H).
IR (KBr): 3360, 3295, 3070, 3050, 3005, 2950, 2930, 2885, 1590, 1482, 1470, 1452, 1372, 1340, 1280, 1245, 1200, 1135, 1120, 1040, 1020, 1000, 980, 960, 932, 910, 900, 885, 850, 825, 810, 70, 735, 695, 665 cm−1.
Hydrochloride:
Yld.=68%, M.p. 225° C. (ethanol),
Anal. (C20H23C12NO2HCl) C, H, Cl, N, O, Example 1b: 2-(3-amino-3-phenyl-pentan-1-yl)-2-phenyl-1,3dioxolane.
[I; R1=R5=C6H5, R2=C2H5, R3=R4=H, W=C(O—CH2—CH2—O)]
a) Prepared from the nitro ketone II.b
Yld.=79%; M.p. 77° C. (hexanes),
TLC: 0.55; S. H.5
b) Yld.=68%; M.p. 64° C.(hexanes)
TLC: 0.25; S. H.5
Anal. (C20H25NO2) C, H, N, O
NMR: 0.60 (t,3H), 1.25–1.95 (m,8H), 3.55–4.10 (m,4H), 7.00–7.60 (m,10H)

Example 1c: 2-(3-amino-3-phenyl-pentan-1-yl)-2-(3,4,5-trimethoxyphenyl)-1,3-dioxolane.
[I; R1=C6H5, R2=C2H5, R3=R4=H, R5=3,4,5(CH3O) 3-C6H2, W=C(O—CH2—CH2—O)]
a) Prepared from the nitro ketone II.c
Yld.=83%; M.p. 112° C. (hexanes),
TLC: 0.45; S. H.3
b) Yld.=58%; M.p. 87° C. (hexanes/ether)
TLC: 0.15; S. H.5
Anal. (C23H31NO5) C, H, N, O
NMR: 0.60 (t,3H), 1.25–1.95 (m,8H), 2.30 (s,9H), 3.55–4.10 (m,4H), 7.00–7.60 (m,7H)

Example 1d: 2-3-amino-3-(4-chlorophenyl)-pentan-1-yl ])-2-(3,4,5-trimethoxvyphenyl)-1,3-dioxolane.
[I; R1=p.Cl-C6H4, R2=C2H5, R3=R4=H, R5=3,4,5(CH3O)3-C6H2, W=C(O—CH2—CH2—O)
a) Prepared from the nitro ketone II.d
Yld.=95%; M.p. 67° C. (hexanes),
TLC: 0.55; S. H.3, b) Yld.=35%, chromatography, M.p. 87° C. (hexanes)
TLC: 0.30–0.40; S. M.2
Anal. (C23H30ClNO5) C, H, Cl, N, 0
NMR 0.70 (t,3H), 1.40 (s,2H), 1.40–2.00 (m,6H), 3.75–4.15
(m,13H), 6.60 (s,2H), 7.25 (s,4H)

Example 1e: 2-3-amino-3-(4-methylohenyl)-pentan-1-yl])-2-(3,4,5-trimethoxyphenyl)-1,3-dioxolane.
[I; R1=p.CH3-C6H4, R2=C2H5, R3=R4=H, R5=3,4,5(CH3O) 3-C6H2, W=C(O—CH2—CH2—O)]
a) Prepared from the nitro ketone II.e
Yld.=91%; M.p. 58° C. (hexanes),
TLC: 0.60; S. H.3
b) Yld.=35%, chromatography (oil)
TLC: 0.10–0.25; S. M.2
Anal. (C24H33NO5) C, H, N, O
3.55–4.05 (m,13H), 6.55 (s,2H), 6.95–7.30 (m,4H)

Example 1.f: 2-3-amino-3-(4-trifluoromethylohenyl)-pentan-1-yl])-2-(3,4,5-trimethoxyphenyl)-1.3-dioxolane.

[I; R1=p.F3C-C6H4, R2=C2H5, R3=R4=H, R5=3,4,5(CH3O)3-C6H2, W=C(O—CH2—CH2—O)]

a) Prepared from the nitro ketone II.f
Yld.=89%; M.p. 75° C. (hexanes)
TLC: 0.35; S. M.1 b) Yld.=95% (oil)
TLC: 0.55; S. M.2
Anal. (C24H30F3NO5) C, H, F, N, O
NMR: 0.70 (t,3H), 1.55 (s,2H), 1.60-1.95 (m,6H), 3.55-4.25
(m,13H), 6.60 (s,2H), 7.30-7.65 (m,4H)

Example 1g: 2-[3-amino-3-(3,4-dichlorophenyl)-pentan-1-yl])-2-(3,4,5-trimethoxvohenyl)-1,3-dioxolane.

[I; R1=3,4(Cl)2-C6H3, R2=C2H5, R3=R4=H, R5=3,4,5-(CH3O)3-C6H2, W=C(O—CH2—CH2-O)]

a) Prepared from the nitro ketone II.g
Yld.=82%; M.p. 59° C. (hexanes);
TLC: 0.25; S. M.1 b) Yld.=92% (oil)
TLC: 0.40; S. M.2
Anal. (C23H29Cl2NO5) C, H, Cl, N, O
NMR: 0.70 (t,3H), 1.35-2.00 (m,8H), 3.60-4.10 (m,13H), 6.60
(s,2H), 7.00-7.50 (m,3H)

Example 2: 4-amino-4-phenyl-1-(3,4,5-trimethoxyphenyl)-hexan-1-ol.

[I; R1=C6H5, R2=C2H5, R3=R4=H,R5=3,4,5(CH3O)3-C6H2, W=CHOH]

A toluene solution containing 200 mmol of aluminum sodium bis(2-methoxyethoxy)hydride is introduced into an anhydrous reactor under a nitrogen atmosphere, and 19.2 g (49.5 mmol) of 4-nitro-4-phenyl-1-(3,4,5-trimethoxyphenyl)hexanone (described in II.c), dissolved in 100 ml of toluene, are then added dropwise and with stirring at room temperature.

The mixture is heated for 4 hours to reflux and then cooled with a bath of ice-cold water; 11.7 ml of 10% (w/v) sodium hydroxide solution are then added cautiously thereto, followed by 14.5 ml of water. The suspension is stirred for 16 hours, 500 ml of water are then added and the mixture is extracted with 3 times 200 ml of ether. The combined ether phases are washed with water and then dried over Na2SO4. The ether is removed by distillation under reduced pressure; the residue, which is the intermediate III (Q=O) corresponding to the starting compound II, is engaged without further treatment in the hydrogenation reaction which follows.

9.1 g (23 mmol) of 4-nitro-4-phenyl-1-(3,4,5-trimethoxyphenyl)hexanol obtained above are introduced with 250 ml of ethanol and 4.0+/−1.0 g of type W 2 activated Raney nickel, suspended in approximately 70 ml of ethanol, into a reactor which is leakproof at an internal pressure of approximately 12 bars. After the appropriate purges have been performed as described in Example 1, hydrogen is introduced on the basis of a pressure of 10 bars, and the suspension is then stirred at room temperature for 72 hours.

The catalyst is then filtered off and the filtrate concentrated under reduced pressure, the residue is dissolved in 100 ml of ether and extracted with 100 ml of 3N hydrochloric acid solution and then with twice 75 ml of N acid.

The acid phases are combined and alkalinized to pH 12 at a temperature below 25° C. with concentrated sodium hydroxide solution (d=1.33) and then extracted with 3 times 100 ml of ether. The combined ether phases are washed with water and dried over Na2SO4; the ether is then removed by distillation under reduced pressure to obtain finally the product in the form of a gum.

Weight=7.6 g; Yld.=90% .
TLC: 0.20 and 0.30 (isomers); S. E.2
NMR 0.90 (m,3H), 1.20 (t,2H), 1.40-2.50 (m,3H), 3.00 (m,1H), 3.50 (q,1H), 3.80 (m,9H), 4.60 (m,1H), 6.55 (s,2H), 7.40 (s,5H), 9.00 (m,2H).

- Hydrochloride:
Yld.=75%; M.p. 85° to 125° C. (ether),
Anal. (C21H29NO4.HCl.0.2C2H5—O—C2H5) C, H, Cl, N, O
IR (KBr): 3310, 2950, 1598, 1513, 1468, 1427, 1335, 1243, 1135, 1012, 848, 770, 707 cm−1.

EXAMPLES 3

General procedure:

stage a: (N-formamide intermediate V.D.2 from compounds of the invention of formula I.D.1)

250 ml of tetrahydrofuran dehydrated over a molecular sieve, 3.9 ml of 99% formic acid (d=1.22-104 mmol) and 16.5 g (102 mmol) of 1,1′-carbonyldiimidazole are introduced into a reactor protected from moisture and under a nitrogen atmosphere.

The solution is stirred for one hour at room temperature (20° C.) and 100 mmol of the compound I.D.1, dissolved in 100 ml of tetrahydrofuran, are then added dropwise thereto. Stirring is maintained for 4 hours at room temperature and the solvent is then removed by distillation under reduced pressure.

The residue is treated with 250 ml of 0.5N hydrochloric acid solution and 200 ml of ether. The acidic aqueous phase is separated after settling has taken place and extracted again with twice 100 ml of ether.

The combined ether phases are washed with water and then dried over Na2SO4. The ether is removed by distillation under reduced pressure and the residual product obtained is used without further treatment or purified, if necessary, by crystallization.

stage b: (compounds I of structures I.D.2 in which R3 =CH3 from N-formamides V.D.2)

400 mmol of aluminum sodium bis(2-ethoxymethoxy)hydride, dissolved in toluene, are introduced into an anhydrous reactor under a nitrogen atmosphere, and 100 mmol of the N-formamide compound V.D.2, dissolved in 400 ml of toluene, are then added dropwise and with stirring at room temperature.

The mixture is stirred at 20° C. for a period of 2 to 8 hours, depending on the compound employed, the progress of the reaction being determined by TLC. At the appropriate time, the mixture is cooled to a temperature below 10° C. and 23 ml of 10% (w/v) sodium hydroxide solution are introduced dropwise, followed by 28 ml of water. After stirring for one hour, the insoluble matter is filtered off and washed with ether on a Buchner lined with a bed of infusorial earth, the combined filtrates are washed with water and dried over Na2SO4 and the solvents are then removed by distillation under reduced pressure. The residue is purified by the appropriate usual methods, excluding, however, acid or alkaline aqueous treatments.

Example 3a: 2-(3-N-methylamino-3-phenyl-pentan-1-yl)-2-(3,4-dichloroohenyl)-1,3-dioxolane.

[I; R1=C6H5, R2=C2H5, R3=CH3, R4=H, R5=3,4(Cl) 2-C6H3, W=C(O—CH2—CH2—O)]

a) Prepared from the compound of Example 1a
Yld.=75% crude (oil)
TLC: 0.30; S. H.3
The product is used without purification.

b) Yld.=55%, chromatography, M.p. 58°-70° C. (hexanes)
TLC: 0.70; S. H.3
Anal. (C21H25Cl2NO2) C, H, Cl, N, O
NMR: 0.55 (t,3H), 1.25 (s,1H), 1.45-1.85 (q,9H), 2.05 (d,3H),
3.60-4.10 (m,4H), 7.10-7.60 (m,8H).
IR (KBr): 3340, 2980, 2750, 2420, 1585, 1500, 1470, 1415, 1380, 1345, 1305, 1225, 1190, 1130, 1090, 1035, 952, 890, 830, 760, 700 cm−1.

Example 3b: 2-(3-N-methylamino-3-phenyl-pentan-1-yl)-2-phenyl-1,3-dioxolane.
[I; R1=R5 =C6H5, R2=C2H5, R3=CH3, R4=H, W=C(O—CH2-CH2—O)]
a) Prepared from the compound of Example 1b
Yld.=65% crude (oil)
TLC: 0.65; S. H.3
The product is used without purification.
b) Yld.=89%; M.p. 58°-70° C. (hexanes)
TLC: 0.50; S. H.3
Anal. (C21H27NO2) C, H, N, O
NMR: 0.60 (t,3H), 1.30 (s,1H), 1.55-1.95 (m,6H), 2.10 (s,3H),
3.65-4.15 (m,4H), 7.15-7.55 (m,10H).
IR (film): 3350, 3090, 3060, 3030, 2970, 2890, 1950, 1890, 1600, 1580, 1490, 1465, 1400, 1380, 1295, 1220, 1190, 1145, 1045, 955, 875, 765, 700 cm−1.

Example 3c: 2-(3-N-methylamino-3-phenyl-pentan-1-yl)-2-(3,5-dimethoxvphenyl)-1,3-dioxolane.
[I; R1=C6H5, R2=C2H5, R3=CH3, R4=H, R5=3,5(CH3O)2-C6H3, W=C(O—CH2—CH2—O)]
a) Prepared from the compound of Example 1c, the intermediate V.D.2 [R5=3,4,5(CH3O)3-C6H2] is obtained
Yld.=82% crude (oil)
TLC: 0.20; S. H.1
The product is used without purification.
b) The reaction is accompanied by the demethoxylation at the 4-position of the radical R5 of the compound.
Yld.=48% M.p. 71° C. (hexanes/ether),
TLC: 0.35; S. E.1
Anal. (C23H31NO4) C, H, N, O
NMR: 0.60 (t,3H), 1.30 (s,1H), 1.50-1.90 (m,6H), 2.05 (s,3H), 3.80 (s,6H), 3.60-4.10 (m,4H), 6.60 (d,3H), 7.10-7.30 (m,5H).
IR (KBr): 3220, 1590, 1450, 1418, 1315, 1233, 1188, 1148, 1054, 1032, 847, 750, 690 cm−1.

Example 3d: 2-3-N-methylamino-3-(4-chlorophenyl)-pentan-1yl]-2-(3,4,5-trimethoxyphenyl)-1,3-dioxolane.
[I; R1=p.Cl-C6H4, R2=C2H5, R3=CH3, R4=H, R5=3,4,5 (CH3O)3-C6H2, W=C(O—CH2—CH2—O)]
a) Prepared from the compound of Example 1d
Yld.=65%; M.p. 94° C. (hexanes),
TLC: 0.50-0.60; S. M.2
b) Yld.=58%; M.p. 94° C. (ether),
TLC: 0.50; S. M.2
Anal. (C24H32ClNO5) C, H, Cl, N, O
NMR: 0.60 (t,3H), 1.10-1.35 (m,H), 1.45-1.85 (m,6H), 2.05
(s,3H), 3.50-4.05 (m,13H), 6.60 (s,2H), 7.25 (s,4H)
IR (KBr): 3000, 1580, 1420, 1400, 1380, 1220, 1120, 1000, 820 cm−1.

Example 3.e.1: 2-[3-N-methylamino-3-(4-methylphenyl)-pentan-1yl]-2-(3,4,5-trimethoxvphenyl)-1,3-dioxolane.
[I; R1=p.CH3-C6H4, R2=C2H5, R3=CH3, R4=H, R5=3.5 (CH3O)3-C6H2, W=C(O—CH2—CH2—O)]
Yld. 85%; M.p. 118° C. (hexanes)
TLC.0.40; S. M.2
b) Yld.=52%; M.p. 95° C. (hexanes)
TLC: 0.30; S. M.2
Anal. (C25H35NO5) C, H, N, O
NMR: 0.60 (t,3H), 1.20-1.85 (m,7H), 2.05 (s,3H), 2.30 (s,3H), 3.650-4.10 (m,13H), 6.60 (s,2H), 7.00-7.30 (m,4H)
IR (KBr): 3000, 1590, 1500, 1450, 1400, 1320, 1220, 1100, 1000, 820 cm−1.

Example 3e.2: 2-[-3-N-methylamino-3-(4-methylphenyl)-pentan-1yl]-2-(3,5-dimethoxyphenyl)-1,3-dioxolane.
[I; R150 p.CH3-C6H4, R2=C2H5, R3=CH3, R4=H, R5=3.5 (CH3O)2-C6H3, W=C(O—CH2—CH2—O)]
By-product obtained in the reduction stage b) in the preparation of the product of the preceding example.
TLC: 0.45; S. M.2
Anal. (C24H33NO4) CHNO
NMR: 0.60 (t,3H), 1.20-1.85 (m,7H), 2.05 (s,3H), 2.30 (s,3H),
3.65-4.10 (m,1OH), 6.60 (m,3H), 7.00-7.30 (m,4H)

Example 3f: 2-[3-N-methylamino-3-(4-trifluoromethylohenyl) pentan-1-yl]-2-(3,4,5-trimethoxvphenyl)-1,3-dioxolane.
[I; R1=p.F3C-C6H4, R2=C2H5, R3=CH3, R4=H, R5=3,4,5(CH3O)3-C6H2, W=C(O—CH2—CH2—O)]
a) Prepared from the compound of Example 1f
Yld.=64%; M.p. 144° C. (ether),
TLC: 0.80; S. M.2
b) Yld.=78%, M.p. 85° C. (hexanes),
TLC: 0.60-0.70; S. M.2
Anal. (C25H32NO5) C, H, F, N, O
NMR: 0.60 (t,3H), 1.30 (s,1H), 1.50-1.80 (m,6H), 2.10 (s,3H), 3.70-4.10 (m,13H), 6.60 (s,2H), 7.35-7.60 (m,4H)
IR (KBr): 2990, 1580, 1460, 1410, 1320, 1220, 1110, 930 cm−1

Example 4: 4-N-methylamino-4-phenyl-1-(3,4,5-trimethoxyphenyl) hexan-1-ol.
I: R1=C6H5, R2=C2H5, R3=CH3, R4=H, R5=3,4,5 (CH3O) 3-C6H2, W=CHOH]
The reaction of stage a) of the preceding Example 3 is applied to 21.5 g (60 mmol) of the 4-aminohexanol of Example 2.
After treatments, 18.4 g (46 mmol) of a mixture of the corresponding N-formamide hexanol and its formate (Yld.=77%) is obtained.
Without further treatment, this mixture, dissolved in 100 ml of anhydrous tetrahydrofuran, is introduced dropwise at room temperature into a solution of 9.9 g (260 mmol) of lithium aluminum hydride in 250 ml of tetrahydrofuran.
The mixture is heated for 5 hours to reflux, cooled to 20° C. with a bath of ice-cold water and then diluted by adding 200 ml of anhydrous ether. 16.0 ml of 10% (w/v) sodium hydroxide solution is then cautiously added dropwise, followed by 20.0 ml of water. The mixture is stirred for 16 hours at room temperature and the insoluble matter is then filtered off. The filtrate is concentrated by distillation under reduced pressure.
The mixture of isomers of the product is obtained in the form of a viscous orange-colored oil.
Weight=8.1 g; Yld.=47%,
TLC: 0.50 and 0.90 (isomers); S. E.2

NMR: 0.90 (m.3H), 1.70 (m,2H), 2.25 (m,4H), 3.20 (s,1H), 3.75–3.90 (m,12H), 4.55–5.10 (m,1H), 6.60 (s,2H), 7.30 (s,5H), 7.75 (m,1H).

-Hydrochloride

Yld.=85%; M.p. 112° C. (benzene/CH2Cl2)

Anal. (C22H31NO4.HCl) C, H, Cl, N, O

IR (KBr) 3420, 2940, 1590, 1503, 1460, 1423, 1328, 1240, 1130, 1010, 840, 764, 700 cm−1.

EXAMPLES 5

General procedure: In an anhydrous reactor maintained under a nitrogen atmosphere, 100 mmol of an intermediate α-(dialkylamino)butyronitrile VII in 150 ml of ether dehydrated over a molecular sieve are introduced dropwise into a solution of 500 mmol of ethylmagnesium bromide in 350 ml of ether.

The introduction is carried out in the course of approximately 30 minutes, and the mixture is then heated to reflux for 2 hours and cooled with a bath of ice-cold water before being precipitated in 400 ml of saturated ammonium chloride solution.

The aqueous phase is separated after settling has taken place and discarded, and the ether phase is extracted twice with 200 ml of N hydrochloric acid solution. The combined acid phases are alkalinized to pH 12 at a temperature below 20° C. with sodium hydroxide solution (d=1.33) and then extracted three times with 250 ml of ether. The combined phases are washed by extraction with saturated sodium chloride solution and then dried over Na2SO4. The ether is removed by distillation under vacuum and the residual crude product is, after chromatographic examination of its purity, either used without further treatment or purified by a suitable method.

The compounds I.D.3 of Examples 5a to 5c are prepared according to this protocol from butyronitriles VII whose preparation is described above.

Example 5a: 2-(3-N,N-dimethylamino-3-phenyl-pentan-1-yl)-2-phenyl-1,3-dioxolane.

[I; R1=R5=C6H5, R2=C2H5, R3=R4=CH3, W=C(O—CH2-CH2O)]

Prepared from the compound VII.a

Yld.=75% crude (oil)

TLC: 0.20–0.30; S. H.5

Anal. (C22H29NO2) C, H, N, O

NMR: 0.60 (t,3H), 1.60–1.90 (m,6H), 2.10 (s,6H), 3.60–4.20

(m,4H), 7.00–7.60 (m,10H)

Example 5b: 2-(3-N,N-dimethylamino-3-phenyl-pentan-1-yl)-2-(3,4,5-trimethoxvohenyl)-1,3-dioxolane.

[I; R1=C6H5, R2=C2H5, R3=R4=CH3, R5=3,4,5(CH3O)-C6H2, W=C(O—CH2—CH2—O)]

Prepared from the compound VII.b

Yld.=48% crude (oil)

TLC: 0.30; S. H.1

Anal. (C25H35NO5) C, H, N, O

NMR: 0.60 (t,3H), 1.60–1.90 (m,6H), 2.10 (s,6H), 3.60–4.20

(m,4H), 6.60 (s,2H), 7.00–7.60 (m,5H)

Example 5c: 2-(3-N,N-dimethylamino-3-phenyl-pentan-1-yl)-2cyclohexyl-1,3-dioxolane.

[I; R1=C6H5, R2=C2H5, R3=R4=CH3, R5=CH(CH2)5, W=C(O—CH2—CH2—O)]

Prepared from the compound VII.c

Yld.=59% crude (oil)

TLC: 0.30–0.40; S. H.3

Anal. (C22H35NO2) C, H, N, O

NMR: 0.60 (t,3H), 1.60–1.90 (m,6H), 2.10 (s,6H), 3.60–4.20

(m,14H), 5.90 (m,H), 7.00–7.60 (m,5H)

(m,14H)

Example 6: 2-3-(N-cyclopropylmethyl-N-methylamino)-3-(4methylphenyl)-pentan-1-y])-2-(3,4,5-trimethoxyphenyl)-1,3dioxolane.

[I; R1=p.CH3-C6H4, R2=C2H5, R3=CH2—CH(CH2)2, R4=CH3, R5=3,4,5(CH3O)3-C6H2, W=C(O—CH2—CH2—O)]

Stage 1: 45 ml of methylene chloride dehydrated over a molecular sieve, followed successively by 5.0 g (11.6 mmol) of the compound prepared in Example 3e.1, and 2.0 ml (1.46 g–14.4 mmol) of triethylamine, are introduced into an anhydrous reactor under a nitrogen atmosphere.

The solution is cooled in an ice bath and 1.2 ml (1.38 g –13.2 mmol) of cyclopropylcarboxylic acid chloride are then introduced dropwise and at a temperature below 10° C.

The mixture is then stirred for 2 hours 30 minutes at room temperature; 50 ml of methylene chloride are then added and the solution is thereafter extracted, successively and each time, with 50 ml of 10% aqueous ammonia solution, water, 10% hydrochloric acid solution, water, saturated sodium bicarbonate solution and finally with water.

The organic phase thus treated is dehydrated over Na2SO4 and the methylene chloride is then evaporated off by distillation under vacuum.

The intermediate N-cyclopropylcarboxamide derivative of formula V.D.3 is obtained in the form of a viscous oil, whose state of purity in the crude state is satisfactory for the product to be employed without further treatment in the next stage.

Weight=5.50 g; Yld.=95%.

TLC: 0.65–0.75; S. M.2

Anal. (C29H39NO6) C, H, N, O

NMR: 0.40–0.90 (m,6H), 1.60–2.40 (m,11H), 3.10 (s,3H), 3.60–4.05 (m,13H), 6.60 (s,2H), 6.90–7.20 (m,4H)

Stage 2: 13.4 ml (d=1.03–48 mmol) of a 70% w/w solution of aluminum sodium bis(2-methoxyethoxy)hydride and 40 ml of toluene dehydrated over a molecular sieve are introduced into an anhydrous reactor under a nitrogen atmosphere. 5.9 g (12 mmol) of N-carboxamide, dissolved in 40 ml of dehydrated toluene, are introduced dropwise and at a temperature below 25° C. in the course of approximately 30 minutes. The mixture is heated and kept refluxing for 40 minutes, then cooled rapidly to approximately 10° C. with a bath of ice-cold water.

2.8 ml of 10% w/v sodium hydroxide solution are then added dropwise and at a temperature below 20° C., followed by 3.5 ml of water. After stirring for one hour, the mixture is filtered on a Buchner lined with a layer of infusorial earth.

The filtrate is evaporated under vacuum; the crude product is obtained in the state of an oil (5.2 g), which is purified by chromatography.

Weight=4.3 g (oil); Yld.=74%,

TLC: 0.15–0.30; S. M.2

Anal. (C29H41NO5) C, H, N, O

NMR: 0.00 (m,2H), 0.30–0.50 (m,2H), 0.60–0.85 (m,4H), 1.60–2.40 (m,14H), 3.70–4.10 (m,13H), 6.65 (s,2H), 7.00–7.35 (m,4H)

Example 7: 2-[3-N,N-dimethylamino-3-(4-methyldhenyl)-pentan-1yl]-2-(3,4,5-trimethoxyphenyl)-1,3-dioxolane.

[I; R1=p.CH3-C6H4, R2=C2H5, R3=R4=CH3, R5=3,5(CH3O)2-C6H3, W=C(O—CH2—CH2—O)]

4.6 g (11.5 mmol) of the propanamine described in Example 3e.2 and 1.95 ml (26 mmol) of 37% formaldehyde solution (d 1.08) are introduced into a reactor equipped with a stirring system; with extremely vigorous stirring, the mixing is weakly exothermic.

1.35 ml (36 mmol) of 99% formic acid (d=1.22) are then added dropwise to the emulsion formed witout exceeding 25° C. The solution then obtained is heated on a waterbath for 30 minutes until gaseous evolution has ceased, and is thereafter cooled and diluted with 50 ml of water and acidified to pH 1 by adding concentrated hydrochloric acid (d=1.18).

The mixture is extracted with twice 25 ml of ether; the ether phases are discarded and the acidic aqueous phase is alkalinized to pH 12 at a temperature below 25° C. by adding concentrated sodium hydroxide solution (d=1.33). The mixture is extracted with 3 times 40 ml of ether; the combined ether phases are washed with saturated sodium chloride solution and then dehydrated over Na2SO4. The ether is removed by distillation. The product is obtained crude in a satisfactory state of purity.

Weight=3.4 g; Yld.=71%
TLC: 0.50–0.65; S. M.2
Anal. (C25H35NO4) C, H, N, O
NMR: 0.75 (t,3H), 1.65-2.25 (m,12H), 3.70–4.10 (m,13H), 6.65
(s,2H), 7.15-7.50 (m,5H)

EXAMPLES 8

General procedure: 100 mmol of a compound of the invention I of structure I.D.1 to be N,N-dimethylated are introduced into a reactor. 17.5 ml (233 mmol) of 37% formaldehyde solution (d=1.08) are added rapidly with vigorous stirring at room temperature.

The reaction is exothermic; a viscous emulsion forms, which is cooled with a ice bath.

11.4 ml of 99% formic acid (d=1.22=302 mmol) are added dropwise without exceeding 15° C. The solution is then heated for one hour and a half on a boiling waterbath until gaseous evolution has completely ceased. 150 ml of water are then added and the mixture is cooled with an icebath and then alkalinized to pH 12 with concentrated sodium hydroxide solution (d=1.33) without exceeding 20° C. The mixture is extracted with 3 times 150 ml of ether. The combined ether phases are washed with saturated NaCl solution and then dried over Na2SO4. The ether is then removed by distillation under vacuum and the residue is either used without further treatment or purified by suitable methods.

The compounds I of structure I.D.3 of Examples 8a to 8e which are described below are prepared according to this experimental protocol from the compounds described in Examples 1.

Example 8 a: 2-[3-(4-chlorophenyl)-3-N,N-dimethylamino-pentan1-yl]-2-(3,4,5-trimethoxyphenyl)-1,3-dioxolane.

[I;R1=Cl-C6H4, R2=R3=R4=CH3R5=3,4,5(CH3O)C6H2, W=C(O—CH2—CH2—O)]
Prepared from the compound I.D.1 of Example 1 d
Yld.=93% crude (oil)
TLC: 0.35–0.45;S. M.2
Anal (C25H34ClNO5) C, H, N, O
NMR: 0.75 (t,3H), 1.65-2.25 (m,12H), 3.70–4.10 (m,13H), 6.65
(s,2H), 7.15-7.40 (m,4H)

Example 8b: 2-[3-N,N-dimethylamino-3-(4-methylphenyl)-pentan1yl]-2-(3,4,5-trimethoxvphenyl)-1,3-dioxolane.

[I: R1=p.CH3-C6H4, R2=C2H5, R3=R4=CH3, R5=3,4,5(CH3O)-C6H2, W=C(O—CH2—CH2—O)]
Prepared from the compound I.D.1 of Example 1e
Yld.=84% crude (oil)
TLC: 0.40; S. M.2
Anal. (C26H37NO5) C, H, N, O
NMR: 0.75 (t,3H), 1.70-2.20 (m,12H), 2.30 (s,3H), 3.65–4.15
(m,13H), 6.65 (s,2H), 7.00-7.30 (m,4H)

Example 8.c: 2-[3-N,N-dimethylamino-3- (4trifluoromethylphenyl)-pentan-1-yl]-1-2-(3,4,5-trimethoxvphenyl)1,3-dioxolane.

[I R1=p.CF3-C6H4, R2=C2H5, R3=R4=CH3, R5=3,4,5(CH3O)-C6H2, W=C(O—CH2—CH2—O)]
Prepared from the compound I.D.1 of Example 1f
Yld =82% crude (oil)
TLC: 0.50–0.60; S. M.2
Anal. (C25H34F3NO5) C, H, N, O
NMR: 0.75 (t,3H), 1.65-2.25 (m,12H), 3.70–4.10 (m,13H), 6.65
(s,2H), 7.15-7.40 (m,4H)

Example 8d: 2-3-(3,4-dichlorophenyl)-3-N,N-dimethylamino pentan-1-v11-2-(3.4,5-trimethoxvphenyl)-1.3-dioxolane.

[I R1 3,4(Cl)2-C6H3, R2 C2H5, R3 R4 CH3, R5=3,4,5(CH3O)-C6H2, W=C(O—CH2—CH2—O)]
Prepared from the compound I.D.1 of Example 1g
Yld.=84% crude (oil)
TLC: 0.80; S. M.2
Anal (C25H33Cl2NO5) C, H, Cl, N, O
NMR: 0.75 (t,3H), 1.65-2.25 (m,12H), 3.70–4.10 (m,13H), 6.65
(s,2H), 7.10-7.40 (m,3H)

Example 8e : 2-(3-N,N-dimethylamino-3-phenyl)-pentan-1-yl)-2-(3,4-dichlorophenyl)-1,3-dioxolane.

[I; R1=C6H5, R2=C2H5, R3=R4=CH3, R5=3,4(Cl)2-C6H3, W=C(O—CH2—CH2—O)]
Prepared from the compound I.D. 1 of Example 1a
Yld.=77% crude (oil)
TLC: 0.60–0.80; S. M.2
Anal. (C22H27Cl2NO2) C, H, N, O
NMR: 0.75 (t,3H), 1.65-2.25 (m,12H), 3.70-4.10 (m,13H), 6.65-7.40 (m,8H)

EXAMPLES 9

General procedure: 100 mmol of 1,3-dioxolane-2-propan-amine compound (I.D.3) to be treated, dissolved in 540 ml of acetone, are introduced into a reactor equipped with a condenser in the reflux position and a stirring system.

500 ml of demineralized water and then 42.5 ml of concentrated hydrochloric acid (d=1.18) are then added with stirring. The mixture is taken to a waterbath and heated for 30 minutes to reflux, then cooled to room temperature; the acetone is then removed by distillation under vacuum.

625 ml of ice-cold water are added to the concentration residue and the resulting mixture is then extracted with 3 times 200 ml of diethylether. The ether phases are discarded and the acid phase is alkalinized to pH 12 with concentrated sodium hydroxide solution (d=1.33). The mixture is extracted with 3 times 200 ml of ether and the combined ether phases are washed with saturated sodium chloride solution and then dried over Na2SO4. After the dehydrating agent is filtered off, the ether is removed by distillation under vacuum.

Depending on its state of purity, which is determined by TLC, the crude product obtained is either purified by suitable methods such as distillation under high vacuum, crystallization or alternatively chromatography, or employed without further treatment in the preparation of an addition salt which is most often a hydrochloride.

The compounds of the invention described in Examples 9a to 9j which follow are obtained according to this protocol from the compounds of the invention I of structure I.D.3 prepared in Examples 5, 6, 7 and 8 above.

Example 9a: 4-(4-chlorophenyl)-4-N,N-dimethylamino-1-(3,4,5-trimethoxyphenyl)-hexan-1-one.

[I R1=p.Cl-C6H4, R2=C2H5, R3=R4=CH3, R5=3,4,5(CH3O)3-C6H2, W=CO]

Preparation from the compound I.D.3 of Example 8a
Yld.=84% crude (oil)
TLC: 0.50–0.60; S. M.2
NMR: 0.85 (t,3H), 1.95–2.40 (m,10H), 2.70–3.10 (m,2H), 3.90
(s,9H), 7.20 (s,2H), 7.35 (s,4H)
-Hydrochloride
Yld.=78%; M.p. 203° C. (ethanol)
Anal. (C23H30ClNO4.HCl) C, H, Cl, N, O
IR (KBr): 3400, 3000, 2500, 2400, 1680, 1580, 1460, 1410, 1320, 1120, 990, 820 cm−1

Example 9b.1: 1-(3,5-dimethoxyphenyl)-4-N,N-dimethylamino-4(4-methylphenyl)-hexan-1-one.

[I; R1=p.CH3 - C6H4, R2=C2H5, R3=R4=CH3, R5=3,5 (CH3O)2-C6H3, W=CO]

From the compound I.D.3 of Example 7.
Yld.=79%, chromatography (oil)
TLC: 0.55–0.65; S. M.2
NMR 0.85 (t,3H), 1.75–2.50 (m,13H), 2.80–3.10 (m,2H), 3.85
(s,6H), 6.60–7.40 (m,7H)
-Hydrochloride
Yld.=72% M.p. 159° C. (CH2Cl2/ether)
Anal. (C23H31NO3.HCl) C, H, Cl, N, O
IR (KBr): 3400, 2900, 2400, 1680, 1580, 1480, 1440, 1320, 1200, 1140, 1060, 1000, 800 cm−1

Example 9b.2: 4-N,N-dimethylamino-4-(4-methylphenyl)-1-(3,4,5-trimethoxyphenyl)-hexan-1-one.

[I; R1=p.CH3 - C6H4, R2=C2H5, R3=R4=CH3, R5=3,4,5 (CH3O)3-C6H2, W=CO]

From the compound I.D.3 of Example 8b
Yld.=70% crystallized M.p. 81° C. (hexanes)
TLC: 0.30–0.50; S. M.2
NMR: 0.85 (t,H), 1.85–2.45 (m,13H), 2.75–3.10 (m,2H), 3.90
(s,9H), 7.10–7.40 (m,6H)
-Hydrochloride
Yld.=85%; M.p. 188° C. (CH2Cl2/ether)
Anal. (C24H33NO4.HCl) C, H, Cl, N, O
IR (KBr): 3400, 3000, 2700, 1670, 1580, 1540, 1500, 1420, 1120, 980, 800 cm−1

Example 9c: 4-N,N-dimethylamino-4-(4-trifluoromethylphenyl)-1-(3,4,5-trimethoxvphenyl)-hexan-1-one.

[I; R1=p.CF3 - C6H4, R2=C2H5, R3=R4=CH3, R5=3,4,5 (CH3O)3-C6H2, W=CO]

From the compound I.D.3 of Example 8c
Yld. =92% crude (oil)
TLC: 0.70–0.80; S. M.2
NMR: 0.85 (t,3H), 1.70–2.45 (m,10H), 2.75–b 3.10 (m,2H), 3.95
(s,9H), 7.210 (s,2H), 7.6? (m,4H)
-Hydrochloride
Yld.=65M.p. 195° C. (ethanol)
Anal. (C24H30F3N04.HCl) C, H, Cl, F, N, O
IR (KBr): 3400, 3000, 2900, 1680, 1580, 1540, 1460, 1410, 1320, 1110, 1000, 820 cm−1

Example 9.d: 4-(3,4-dichlorophenyl)-4-N,N-dimethylamino-1-( 3,4,5-trimethoxvphenyl)-hexan-1-one.

[I; R1=3,4 (Cl)2-C6H4, R2=C2H5, R3=R4=CH3, R5=3,4,5 (CH3O)3-C6H2, W=CO]

From the compound I.D.3 of Example 8d
Yld.=86% crude (oil)
TLC: 0.80–0.90; S. M.2
NMR: 0.85 (t,3H), 1.70–2.40 (m,10H), 2.70–3.00 (m,2H), 3.90
(s,9H), 7.10–7.60 (m,5H)
-Hydrochloride
Yld.=70% M.p. 153° C. (ethanol)
Anal. (C23H29Cl2NO4.HCl) C, H, Cl, N, O
IR (KBr): 3400, 2900, 2600, 1680, 1560, 1460, 1410, 1380, 1120, 990 cm−1

Example 9e: 4-dimethylamino-1,4-diphenyl-hexan-1-one.

[I; R1 =R5 =C6H5, R2=C2H5, R3=R4=CH3, W=CO]

From the compound I.D.3 of Example 5a
Yld =38% B.p. 163°–185° C/7Pa
TLC: 0.25; S. H.3
Anal. (C20H25NO) C, H, N, O
NMR: 0.80 (t,3H), 1.65–2.60 (m,10H), 2.70–3.20 (m,2H), 6.95–7.65 (m,8H), 7.75–8.10(m,2H)
IR (film): 3065, 2980, 2945, 2885, 2835, 2795, 1682, 1597, 1578, 1447, 1317, 1290, 1233, 1208, 1180, 1001, 981, 759, 741, 700, 691.

Example 9f 4-N,N-dimethylamino-4-phenyl-1-(3,4,5-trimethoxyphenyl)-hexan-1-one.

[I.C.3 R1=C6H5, =R2=C2H5, =R3=R4=CH3, R5=3,4,5(CH3O)3-C6H2, W=CO)

From the compound I.D.3 of Example 5b
Yld.=55% chromatographed (oil)
TLC: 0.30; S. B
Anal. (C23H31NO4) C, H, N, O
NMR: 0.90 (t,3H), 1.80–3.40 (m,6H), 2.20 (s,6H), 3.85 (s,9H),
7.20 (s,2H), 7.35 (s,5H)
IR (film) 3100-2780, 1677, 1584, 1502, 1459, 1412, 1330, 1231, 1188, 1154, 1128, 1005, 855, 763, 703, 680 cm−1

Example 9.g: 1-(3,4-dichlorophenyl)-4-N,N-dimehthylamino-4-phenyl-hexan-1-one.

[I; R1=C6H5, R2=C2H5, R3=R4=CH3, R5=3,4 (Cl) 2-C6H3, W=CO]

From the compound I.D.3 of Example 8e
Yld.=96% crude (oil)
TLC: 0.60; S. E.1
NMR: 0.80 (t,3H), 1.60–3.20 (m,12H), 7.20-8.10 (m,8H)
-Hydrochloride
Yld.=85%, M.p. 160° C. (methanol/ether)
Anal. (C20H23Cl2NO.HCl) C, H, Cl, N, O
IR (KBr): 3650, 3405, 3060, 3010, 2900, 2660, 2600, 2570, 2450, 1670, 1640, 1610, 1580, 1550, 1515, 1425, 1405, 1385, 1350, 1340; 1320, 1292, 1278, 1252, 1200, 1155, 1135, 1080, 1043, 1030, 1020, 1000, 915, 900, 845, 825, 810, 765, 730, 705, 670 cm−1.

Example 9h: 1-cyclphexyl-4-N,N-dimethylamino-4-phenylhexan-1one.

[I; R1=C6H5, R2=C2H5, R3=R4=CH3, R5=CH (CH2)5, W=CO]

From the compound I.D.3 of Example 5c
Yld =26% distilled (oil) B.p. 153°-164° C/13Pa
TLC: 0.30; S. H.5
Anal. (C20H31NO) C, H, O, N
NMR: 0.80 (t,3H), 0.90-2.50 (m,17H), 2.15 (s,6H), 7.40 (m,5H)
IR (film): 1707, 1445, 1145, 1000, 758, 700 cm−1

Example 9i: N-cyclopropylmethyl-4-N-methylamino-4-(4-methylphenyl)-1-(3,4,5-trimethoxvphenyl)-hexan-1-one.
[I; R1=p.CH3-C6H4, R2=C2H5, R3=CH3, R4=CH2—CH (CH2) R5=3,4,5(CH3O)3-C6H2, W=CO]

From the compound I.D.3 of Example 6
Yld.=92% crude (oil)
TLC: 0.60-0.75; S. M.2
NMR: 0.00 (m,2H), 0.30-0.60 (m,2H), 0.70-1.00 (m,4H}, 1.70-2.45
(m,14H), 2.65-3.00 (m,2H), 3.90 (d,9H), 7.00-7.50 (m,6H)
-Hydrochloride
Yld.=75%; M.p. 112° C. (methanol)
Anal. (C27H37N04.HCl) C, H, Cl, N, O
IR (KBr): 3400, 2950, 2150, 1660, 1580, 1500, 1450, 1410, 1330, 1100, 950, 810 cm−1

Example 10: N-allyl-1,4-diphenyl-4-N-methylaminohexan-1-one
[I; R1=R5=C6H5, R2=C2H5, R3=CH3, R4=CH2—CH=CH2, W=CO]

First stage: 2-(3-N-allylamino-3-phenyl-pentan-1-yl)-2-phenyl-1,3-dioxolane.
[I; R1=R5=C6H5, R2=C2H5, R3=H, R4=CH2—CH=CH2, In a 250 ml reactor protected from moisture, 2.73 ml (32 mmol) of allylbromide (d=1.398) are added to a solution of 10.0 g (32 mmol) of compound I (example 1b) in 160 ml of acetonitrile.

The solution is heated to reflux for 24 hours, then the acetonitrile is removed by vacuum distillation.

The crude residue is purified by chromatography on a silica column, eluting with a methylene chloride/methanol mixture.
Weight=9.5g (yellow oil) Yld.=84%
TLC: 0.9; S. M.2
NMR 0.65 (t,3H), 1.20 (m,1H ch.), 1.50-1.85 (m,6H), 2.70-2.90
(m,2H), 3.60-4.05 (m,4H), 4.90-5.30 (m,2H), 5.60-6.10 (m,1H), 7.00-7.50 (m,10H)

Second stage: 2-(N-allylamino-3-N-methylamino-3-phenyl pentan-1-yl)-2-phenyl-1,3-dioxolane.
[I; R1=R5=C6H5, R2=C2H5, R3=CH3, R4=CH2—CH=C(O—CH2—CH2—O)]

In a 100 ml flask, 8.9 g (25 mmol) of the previous stage propanamine are thoroughly mixed with 4.4 ml of a 37% formaldehyde solution (d=1.08) to give an emulsion 2.92 ml of 99% formic acid (d=1.22) are added to the obtained emulsion. The orange-yellow solution is heated on a boiling water-bath for 45 minutes, then poured into 100 ml of ice-cold water.

The mixture is acidified to pH 1 by a concentrated solution of hydrochloric acid, then extracted with twice 75 ml of ether.

The ethereal phases are discarded, the acid aqueous phase is made alkaline to pH 12 (with a concentrated sodium hydroxide solution), keeping the temperature below 20° C. The mixture is extracted with three times 70 ml of ether. The combined ethereal phases are washed with a sodium chloride saturated solution then dried over sodium sulfate. Ether is evaporated. The orange yellow oily residue (7.0 g) is used such in the following stage.

Third stage: N-allyl-1,4-diphenyl-4-N-methylaminohexan-1-one
[I; R1=R5=C6H5, R2=C2H5, R3=CH3, R4=CH2—CH=CH2, W=CO]

Into a 500 ml flask, 7.0 g (19.2 mmol) of the allylamine obtained in the above stage 2 and 8.2 ml of concentrated hydrochloric acid (d: 1.18) in 200 ml of an 1:1 acetone/water mixture (v/v) are introduced.

The solution is heated and kept 30 minutes to reflux, then acetone is removed by vacuum distillation.

The residual aqueous phase is extracted twice with 100 ml of ether. The ethereal phases are discarded, the acidic aqueous phase is made alkaline with a concentrated sodium hydroxyde solution then extracted with thee times 70 ml of ether. The combined ethereal phases are washed with a sodium chloride saturated solution, then dried over sodium sulfate.

After removal of the ether by distillation, 6.1 g of an orange residual oil is obtained and purified by chromatography. The elution with a methylene chloride/acetone mixture gives the pure product as a pale yellow oil.
Weight=5.7 g; Yld.=92.5%.
TLC: 0.70; S. C.2
NMR: 0.85 (t,3H), 1.80-2.40 (m,4H), 2.30 (m,3H), 2.80-3.20
(m,4H), 4.90-5.30 (m,2H), 5.60-6.00 (m,1H), 7.10-8.00 (m,10H)
IR (film): 3000, 1680, 1440, 1280, 1200, 990, 905, 760, 740, 700 cm−1

Example 11: N-allyl-1.4-diphenyl-4-N-methylaminohexan-1-ol
[I; R1=R5 =C6H5, R2=C2H5, R3=CH3, R4=CH2—CH=CH2, W=CHOH]

Into a reactor protected from moisture, 150 ml of anhydrous methanol then 5.0 g (15.5 mmol) of the hexanone prepared at the above example 10 (stage 3), are introduced.

To the so obtained orange-yellow solution are added 0.75 g (19.7 mmol) of sodium borphydride, under stirring and at the ambient temperature. After the gaseous evolution, the pale yellow solution is kept under stirring at 20° C. for one hour then 15.5 ml of water are added.

The mixture is stirred 20 minutes then the methanol is removed by vacuum distillation. After the addition of 100 ml of water to the residue of the distillation, the latter is extracted with twice 75 ml of ether.

The ethereal phases are washed with a saturated sodium chloride solution then dried over sodium sulfate.

Ether is removed by distillation. The crude oily residue (4.9 g) is purified by chromatography. The elution with methylene chloride progressively enriched with methanol gives, with the CH2Cl2/CH3OH 95-5 (v/v) mixture, the isomers of the compound as a colorless viscous oil.
Weight=4.30g; Yld.=86%
TLC: 0.80; S. M.2
Anal. (C22H29NO) C, H, N, O
NMR: 0.60-0.90 (m,3H), 1.60-2.20 (m,9H), 2.80-3.10 (m,2H),
3.40-3.70 (m,1H ch.), 4.50-4.70 (m,1H), 4.90-5.20 (m,2H), 5.50-6.00 (m,1H), 7.10-7.50 (m,10H)
IR (film): 3400, 3000, 1490, 1450, 990, 740, 700 cm−1

Example 12: 2-(3-N,N-dimethylamino-3-phenyl-pentan-1-yl)-2-phenyl-1,3-dithiolane.

[I; R1=R5=C6H5, R2=C2H5, R3=R4=CH3, W=C(S—CH2—CH2-S)]

Into a 25 ml flask protected from moisture and under a nitrogen atmosphere, 5.0 g (17 mmol) of 4-dimethylamino-1,4-diphenylhexanone prepared in example 9e and 8.3 ml (d=1.233−109 mmol) of ethanedithiol are introduced.

8.3 ml (d=1.154−67 mmol) of boron trifluoride etherate are added to the stirred orange solution. The blackish solution is stirred at the ambient temperature for 24 hours then poured into 100 ml of icy-water, made alkaline up to pH 12 with a concentrated sodium hydroxide solution, then extracted with twice 100 ml of ether.

The combined ethereal phases are washed with a saturated sodium chloride solution then dried over Na2SO4.

The ether is removed by vacuum distillation and the crude residue (8.0 g) is purified by chromatography. Elution with a methylene chloride/methanol mixture gives 6.0 g of pure product as an orange colored oil.

Yld.=95%; TLC: 0.50–0.70; S. M.2

NMR: 0.70 (t,3H), 1.70–2.50 (m,6H), 2.00(s,6H), 3.0514 3.50

(m,4H), 7.10–7.80 (m,10H)

IR (film): 2900, 2750, 1480, 1440, 1280, 1000, 760, 740, 700cm−1

-Hydrochloride

In a 50 ml flask protected from moisture, 3.0 g (8 mmol) of the above obtained product are added to an excess of chlorhydric ethanol. After two hours under stirring at the ambient temperature, the solvents are removed by vacuum distillation and the amorphous residue is mixed with 10 ml of ethylacetate. The insoluble residue is filtered, dried under vacuum up to constant weight.

Weight=3.0g; Yld.=92%; M.p. 204° C.

Anal. (C22H29NS2, HCl) C, H, Cl, N, S

PHARMACOLOGICAL STUDIES

The methods performed and the results obtained which enable the properties of the compounds of the invention to be demonstrated are reported below. These are essentially:

the inhibitory activity in rats of castor oil-induced diarrhea, a study of the activity of the compounds with respect to gastrointestinal transit in rats, a study in mice of the ability of the compounds to cause so-called dependency behaviour.

1 - Antidiarrheal activity in rats.

This test is performed by studying the activity of the test compounds with respect to the diarrhea phenomenon caused in animals by the administration of castor oil.

The method consists in administering the test product in solution orally, one hour before the administration, also oral, of 1.0 ml of castor oil per animal.

The animals are then observed, and the number of rats which emit liquid stools is determined on an all-or-nothing basis every hour during the seven hours following administration of the diarrheal agent.

In practice, the products of the invention were administered at several doses so as to be able to determine their ED50 after 3 hours, which represents the effective dose in mg/kg of product enabling the effect of castor oil to be inhibited at this time in 50% of animals treated. The results are presented in Table 1 below, loperamide (INN) and morphine being studied by way of a comparative product and a reference product.

TABLE 1

| Antidiarrheal activity of the compounds | |
|---|---|
| Compound | ED 50 mg/kg at 3 h. |
| Ex. 3.c | 16.0 |
| Ex. 3.f | 6.0 |
| Ex. 9.a | 6.0 |
| Ex. 9.b.2 | 2.0 |
| Ex. 9.c | 15.0 |
| Ex. 9.g | 3.0 |
| Ex. 10 | 24.2 |
| Ex. 12 | 23.1 |
| Loperamide (INN) | 0.20 |
| Morphine | 0.83 |

2 - Activity with respect to intestinal transit.

The test is carried out according to the technique described by Green A. F., J. Pharmacol., 1959, 14, 26-34. It consists in determining in rats the distance travelled in the animal's intestine by a semi-solid meal after a specified time.

The test products are administered orally one hour before gavage of the animal with a semi-solid meal containing vegetable charcoal as a tracer. 15 minutes after the administration, the animal is sacrificed and the distance travelled in the intestine by the meal is expressed in relation to the total length.

This ratio, for the treated animals, is compared with that observed in control animals receiving only the meal.

In this test, the products of the invention were administered on the basis of 30 mg/kg and the results expressed as a percentage change relative to the controls, the ratio being positive when transit is accelerated and negative when it is slowed down; they are presented in Table 2, in which, for morphine and loperamide (INN) which are employed as comparative products, the results are expressed differently, namely as their ED50 which is the effective dose in mg/kg capable of slowing down transit in the animal by 50%.

TABLE 2

| Activity with respect to intestinal transit in rats | | |
|---|---|---|
| Compound | Dose | Activity |
| Ex. 3.c | 30 mg/kg | −3% |
| Ex. 3.f | 30 mg/kg | −17% |
| Ex. 9.a. | 30 mg/kg | −15% |
| Ex. 9.b.2 | 30 mg/kg | −14% |
| Ex. 9.c | 30 mg/kg | +2% |
| Ex. 9.g | 30 mg/kg | −25% |
| Ex. 10 | 30 mg/kg | −6% |
| Ex. 12 | 30 mg/kg | −12% |
| Loperamide | 1.79 mg/kg | −50% |
| Morphine | 10 mg/kg | −50% |

These results show that the effect on transit caused by the compounds of the invention may be considered to be insignificant, or even zero as, for example, for the products of Examples 3.c and 9.c.

3 -Study of the "dependency" state caused by the compounds.

This test is carried out in mice, and consists in administering the test compounds to the animal orally and in solution in a volume of 0.4 ml per 20 g of animal's body weight.

The study of the compounds of the invention consists in administering them in successive and increasing doses for two days to each a total of 360 mg/kg, complying with the following sequences:

t 0 - 10 mg/kg; t 1 h and t 2 h - 25 mg/kg; t 4 h and 6 h - 50 mg/kg; t 24 h and 26 h - 100 mg/kg.

At t 28 h, the animals receive 100 mg/kg of naloxone intraperitoneally. They are then placed in cages and observed for 30 minutes; those which perform jumps are considered to be in a state of addiction and are counted.

The results are expressed as the number of animals exhibiting this state relative to the total number of animals of the test batch.

Loperamide (INN) and morphine tried in this test are too toxic at the administration doses described above. Lower doses were hence administered in order to define their ED50, which is the total effective dose in mg/kg over 26 hours which causes a dependency phenomenon of one half of the animals employed in the test. These results are presented in Table 3.

TABLE 3

| Study of the dependency phenomenon in mice | | |
|---|---|---|
| Compound | Dose | % dependence |
| Ex. 3.f | 360 mg/kg | 0% |
| Ex. 9.b.2 | 360 mg/kg | 10% |
| Loperamide | 75 mg/kg | 50% |
| Morphine | 53 mg/kg | 50% |

This study provides a convincing demonstration of the safety of the compounds. Thus, the preferred compounds of the invention have almost zero activity at doses 5-7-fold greater than those Loperamide (INN) and morphine cause dependency phenomena in 50% of animals treated.

Therefore, they are especially well suited for the treatment of diarrheal states without however disturbing the intestinal transit, or during extended treatment, without inducing any dependency effects.

The propanamines of the invention are presented in pharmaceutical forms, the single-dose preparations of which usually contain between 1 and 500 mg, and more especially between 5 and 200 mg, depending on the intensity of the condition to be treated. The daily therapeutic dosages can be divided into several doses totaling between 5 and 2,000 mg of product per day. However a daily dosage of 50 to 500 mg of product divided into two to four doses is generally satisfactory.

The pharmaceutical forms can be, as non-limiting examples, tablets, dragees, capsules, powders, solutions, suspensions, gels or suppositories. These forms are prepared with the propanamines in their base form or alternatively in their salified form.

In general, in the "solid" forms, the active principle represents from 5 to 90% by weight of the total of the finished form, whereas the pharmaceutically suitable excipients represent from 95 to 10%. For the forms which are liquid or are considered as such, the quantity of active principle is between 0.1 and 10% by weight of the finished form, whereas the pharmaceutically suitable excipients represent from 99.9 to 90% by weight of this form.

Formulation examples and their use for the administration of the products of the invention in pharmaceutical forms are presented.

| Injectable isotonic solution | |
|---|---|
| Formula: | |
| Compound of Example 9 b.2 (hydrochloride) | 10 mg |
| Sodium chloride | 9 mg |
| Distilled water q.s. | 1.0 ml |

Preparation: the isotonic solution is distributed in ampoules of suitable volume which, after sealing, are sterilized by thermal means known per se, or alternatively the solution is sterilized by filtration and distributed in ampoules which are then sealed, all of these operations being carried out under a sterile atmosphere.

In the latter case, it is preferable to add 1% of benzyl alcohol as a bacteriostatic agent, equivalent to 10 mg of this alcohol per ml of solution, to the formula described.

| Tablets | |
|---|---|
| Formula | |
| Active substance of Example 3.f | 10.0 to 50.0 mg |
| Polyvinylpyrrolidone | 20.0 mg |
| Carboxymethylstarch | 8.0 mg |
| Magnesium stearate | 2.0 mg |
| Colloidal silica | 0.4 mg |
| Lactose (q.s.) | 200.0 mg |

Preparation

The active principle is mixed with the lactose and then granulated with the polyvinylpyrrolidone in solution. The particles are dried and sieved through a screen of aperture 1 mm. The carboxymethylstarch is mixed with the colloidal silica and then added to the granules. The latter are then mixed intimately with the magnesium stearate and thereafter tableted on the basis of 200.0 mg per dosage unit.

| Gelled suspension to be taken by mouth | |
|---|---|
| Formula | |
| Active substance of Example 9.b.2 (hydrochloride) | 0.20 to 0.50 mg |
| Hydroxypropylcellulose | 2.00 g |
| Sodium saccharinate | 0.01 g |
| Sorbitol syrup, 70% (w/v) | 25.00 g |
| Natural strawberry flavoring | 0.50 g |
| Preservative | 0.10 g |
| Purified water, q.s. | 100.0 g |

Preparation

The preservatives and the sodium saccharinate are dissolved in water and then, with stirring, the hydroxypropylcellulose is added while dispersion of the latter is effected. Stirring is maintained until a gel is obtained, to which the sorbitol syrup and then finally the flavoring are added, still with stirring.

We claim:

1. A propanamine of general formula (I)

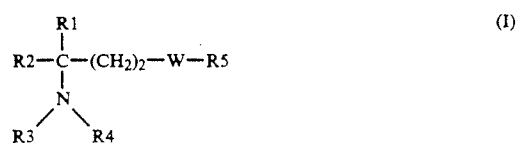

in which:

R1 is a phenyl radical optionally mono-, di- or trisubstituted in an identical or different manner with halogen atoms, or lower alkyl, lower haloalkyl or lower alkoxy radicals;

R2 is a lower alkyl radical,

R3 and R4 are a hydrogen atom or a lower alkyl, lower alkenyl or lower cycloalkylalkyl radical, R5 is a 5- to 7-membered cycloalkyl radical or a phenyl radical, and W represents a heterocycle $C[Q-(CH_2)_n-Q]$ in which Q is an oxygen or sulfur atom and n is 2 or 3, and their acid addition salts with pharmaceutically acceptable acids.

2. A compound according to claim 1 wherein n is 2.

3. A compound according to claim 1 wherein R3 is methyl and R4 is hydrogen.

4. A compound according to claim 1 wherein R3; and R4 are each methyl.

5. A compound according to claim 1 wherein Q is an oxygen atom.

6. An antidiarrheal pharmaceutical composition comprising a compound according to claim 1 and a pharmaceutically acceptable excipient.

* * * * *